United States Patent [19]

Miyamura et al.

[11] Patent Number: 5,500,342
[45] Date of Patent: Mar. 19, 1996

[54] METHOD FOR DETERMINING SUGAR CHAIN STRUCTURE

[75] Inventors: Tsuyoshi Miyamura, Nishinomiya; Mutsumi Sano, Otsu; Akihiro Kondo, Akashi; Ikunoshin Kato, Uji, all of Japan

[73] Assignee: Takara Shuzo Co., Ltd., Kyoto, Japan

[21] Appl. No.: 288,768

[22] Filed: Aug. 11, 1994

[30] Foreign Application Priority Data

Aug. 23, 1993 [JP] Japan .................................. 5-227877
Jul. 8, 1994 [JP] Japan .................................. 6-179748

[51] Int. Cl.$^6$ .............................. C12Q 1/00; C12Q 1/54; C07G 3/00; C07H 19/00
[52] U.S. Cl. .................................. 435/4; 435/14; 435/18; 435/24; 435/7.91; 435/810; 536/18.5; 536/22.1; 536/25.4
[58] Field of Search .................... 435/4, 18, 14, 435/24, 7.91, 74, 810; 536/18.5, 22.1, 25.4

[56] References Cited

U.S. PATENT DOCUMENTS

| | | | |
|---|---|---|---|
| 4,918,009 | 4/1990 | Nilsson | 435/18 |
| 4,975,533 | 12/1990 | Kondo et al. | 536/55 |
| 5,100,778 | 3/1992 | Rademacher et al. | 435/18 |
| 5,260,433 | 11/1993 | Englehardt et al. | 435/6 |
| 5,274,086 | 12/1993 | Kasai et al. | 536/17.6 |
| 5,284,558 | 2/1994 | Linhardt et al. | 536/18.5 |
| 5,340,453 | 8/1994 | Jackson | 204/182.8 |

OTHER PUBLICATIONS

Sano et al, Proc. Natl. Acad. Sci. USA, vol. 89, pp. 8512–8516, Sep. 1992.

Ito et al, Eur. J. Biochem, vol. 215, pp. 171–179, 1993.

Takegawa et al, Biochem Int. (Abstract), vol. 24(5), pp. 849–855, Jul. 1991.

Tomiya et al, Anal Biochem, vol. 171, pp. 73–90, (1988).

Hase et al, J. Biochem., vol. 95, pp. 197–203 (1984).

Tsuda et al., "Comparative Structural Study of N–Linked Oligosaccharides of Urinary and Recombinant Erythropoietins", Biochemistry 1988, 27, 5646–5654.

Edge et al., "Fast Sequencing of Oligosaccharides: The Reagent–Array Analysis Method", Proc. Natl. Acad. Sci. USA, vol. 89, pp. 6338–6342, Jul. 1992, Biochemistry.

Primary Examiner—Michael G. Wityshyn
Assistant Examiner—Louise N. Leary
Attorney, Agent, or Firm—Wenderoth, Lind & Ponack

[57] ABSTRACT

A more exact, reliable, and simple method for determining the structure of a sugar chain, a kit to be used for this method, and novel oligosaccharides useful for the method as standard sugar chains are provided. The method for determining the structure of an N-acetyllactosamine type of sugar chain is characterized by determining the site of linkage and the mode of linkage of sugar residues at the non-reducing terminal side of a β-N-acetylglucosamine residue linked to an α-mannose residue in M3 core by means of detecting the presence of the β-N-acetylglucosamine residue after enzymatic or chemical treatment of the sugar chain. The kit for determining the structure of an N-acetyllactosamine type of sugar chain is characterized by containing at least one of the oligosaccharides represented by the chemical formula 1. The oligosaccharide is represented by the chemical formula 4.

22 Claims, 19 Drawing Sheets

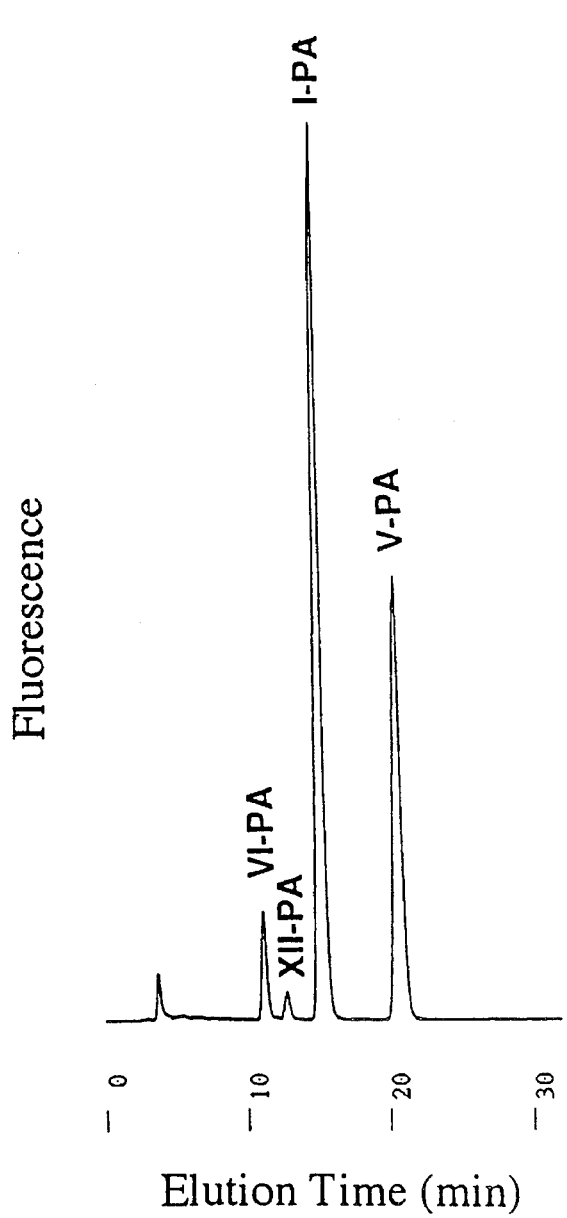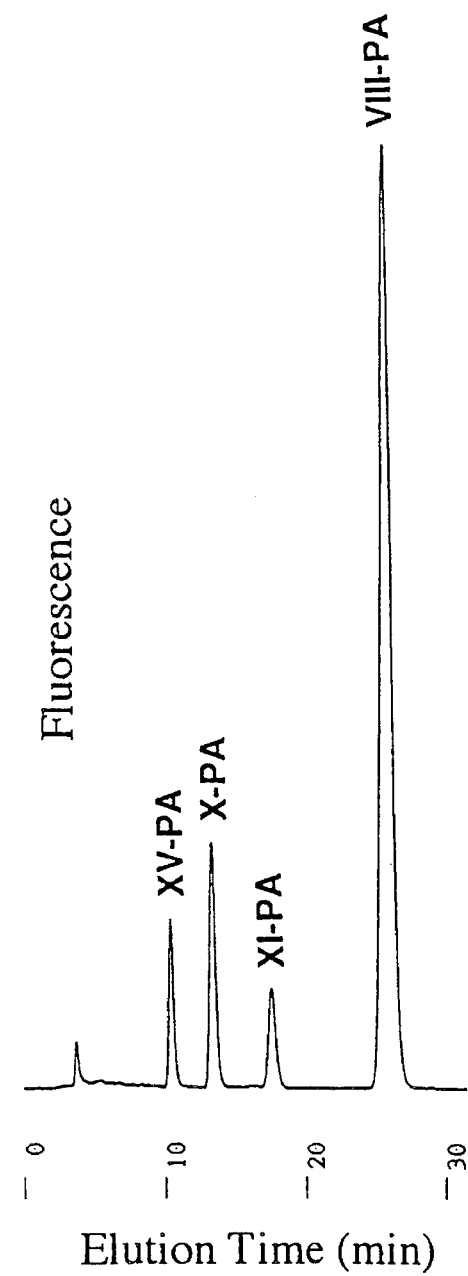
Fig. 3
Fig. 4

Chemical Shift (ppm)

Chemical Shift (ppm)

METHOD FOR DETERMINING SUGAR CHAIN STRUCTURE

FIELD OF INDUSTRIAL APPLICATION

The present invention relates to a method for determining sugar chain structures, a kit to be used for said method and novel oligosaccharides. The present invention, in particular, relates to a method for determining the structure of an N-acetyllactosamine type of sugar chain, a kit to be used for said method, and novel oligosaccharides.

PRIOR ART

Recently, much evidence has been presented for proving the fact that the sugar chains per se function in the recognition of cells, adhesion of cells or metastasis of cancer and, therefore, the structural analysis of the sugar chain in glycoconjugates including glycoproteins and glycolipids is becoming more and more important. In the prior art, the chain structure was analyzed by various analytical methods including methylation analysis, periodate oxidation, enzymatic digestion, nuclear magnetic resonance spectroscopy, and mass spectrometry. In addition, it has become possible to analyze sugar chains by high-performance liquid chromatography (HPLC), which has been rapidly developed in recent years. A method for the fluorescence labeling of sugars with 2-aminopyridine has been developed by Hase et al. [*Journal of Biochemistry*, 95, 197–203 (1984); hereinafter, this method and pyridylamino sugar will be referred to as PA-method and PA-sugar, respectively], and the combination of pyridylamination with HPLC using two kinds of columns, i.e. so-called two-dimensional mapping method makes it possible to analyze many oligosaccharides sensitively [*Analytical Biochemistry*, 171, 73–90 (1988)].

However, it is impossible to distinguish sugar chains having the same elution position or elution positions which are very close to each other in the two kinds of columns from each other by this method. Further, this method is ineffective for sugar chains not mentioned in the map, particularly, for those having sialic acid residues, and it is thus unsuitable for the determination of the structure of a sugar chain having an unknown structure.

When the structure of a sugar chain is to be determined by a method, which combines any labeling method with any separation method, such as the combination of pyridylamination with HPLC, all of the possible sugar chains should be available for the standard sugar chains with the structures determined by any method, and moreover, they should be separated and identified by the separation methods, but this must be impossible because of the diversity of sugar chain structures. Thus, digestion with exoglycosidases with limited substrate specificities is usually used for determination of sugar chain structures. In this method, the products from exoglycosidase digestion are separated and identified by chromatography [see, for example, E. Tsuda et al., *Biochemistry*, 27, 5646–5654 (1988)]. The digestion with the exoglycosidase with limited substrate specificity will be hereinafter referred to as "enzymatic digestion".

Exoglycosidases can recognize a kind of sugar residue at the non-reducing terminus of a sugar chain and the anomeric isomers of the sugar residue (α and β), and the exoglycosidases with limited substrate specificities can recognize the position of the linkages also. Here the combination of the anomeric isomers and the position of the linkage, e.g.: α-2,3-linkage or β-1,4-linkage will be referred to as the "mode of linkage." For example, β-galactosidase from *Diplococcus pneumoniae* recognizes only Galβ-1,4-linkage at a non-reducing terminus and hydrolyzes it, and β-galactosidase from jack beans recognizes β anomeric isomer of Gal at a non-reducing terminus and releases it. The kind of a sugar residue and its mode of linkage at the non-reducing terminus of a sugar chain can be estimated by consideration of the substrate specificities of exoglycosidases. For example, when a sugar chain sample can be digested with β-galactosidase from *D. pneumoniae*, it can be estimated that the sugar chain has a Galβ-1,4-linkage at the non-reducing terminus.

The enzymatic digestion is generally conducted stepwise. For example, when a sugar chain sample 1 is digested with an enzyme A, a sugar chain 2 is obtained as the digestion product. The sugar chain 2 is recovered and then digested with an enzyme B to give a sugar chain 3, which is further digested with an enzyme C. Such a process is repeated. Therefore, the technique of structural analysis by the enzymatic digestion has the serious defect that it requires a time consuming step for the recovery of the digestion product even though the techique can distinguish a difference in a fine structure.

To overcome this defect, a technique of systematically conducting the enzymatic digestion of the sugar chain to estimate the structure thereof has been developed [U.S. Pat. No. 5,100,778 and C. J. Edge et al., *Proc. Natl. Acad. Sci. U.S.A.*, 89, 6338–6342 (1992)].

This technique is characterized by a series of operations comprising:

1. division in equal parts of a sugar chain sample the structure of which is to be determined,
2. complete digestion of the respective parts with a series of different enzyme mixtures,
3. chromatographic analysis of a mixture comprising each of the reaction mixtures,
4. comparison of the analytical spectrum, namely, the elusion position and intensity of each peak obtained by the chromatographic analysis with the spectrum that is theoretically calculated from the sugar chain structure in data bases, and
5. estimation of the structure of a sugar chain sample by making a choice of structure giving an analytical spectrum that is statistically most close to that of the sugar chain sample among those in the data base.

This technique requires only one chromatographic analysis and it does not require the recovery of sugar chains, so the structural analysis of the sugar chain by the enzymatic digestion has been simplified and expedited by this technique.

However, since this technique is based on the approximation of the experimental spectrum to the theoretical spectrum, there is a possibility that the estimated structure might be erroneous or two or more structures might be estimated, when the experimental spectrum is fundamentally distant from the theoretical one or when two or more sugar chains having identical or remarkably similar theoretical spectra are found in the data base. For example, according to C. J. Edge et al. [*Proc. Natl. Acad. Sci. U.S.A.*, 89, 6338–6342 (1992)], even when a sugar chain having a simple structure of the following formula 5

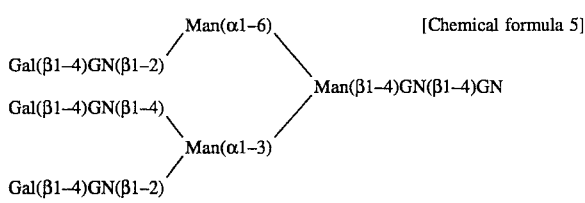

[Chemical formula 5]

is analyzed by this technique, two structures are theoretically estimated for it in equal probability from the analytical results and it is impossible to determine the true structure thereof. Edge and his co-workers say that this problem might be solved to some extent by adding an enzyme having a more exact linkage specificity to the enzyme mixture. However, when the number of enzymes to be used increases, the number of required enzyme mixtures also increases, therefore this technique is not practical, and moreover, the number of such specific enzymes is limited, and it is practically impossible to establish an enzyme mixture capable of distinguishing all of the possible structures of sugar chains.

This technique has another serious defect. Namely, the structures of many sugar chains, particularly asparagine-linked sugar chains, are not linear but complicatedly branched. Therefore, one sugar chain has two or more non-reducing termini, i.e. branches. Even when the kinds and number of the sugar residues and the mode of linkage of them are determined by the technique, it is impossible to determine which branches have the sugar residues if all of the branches do not have the residue. Thus the structure cannot be identified in some cases. In addition, this technique is very sensitive to factors which disturb the experimental spectrum, such as reduction in the activity of the enzyme used, contamination with a very small amount of an unexpected enzyme activity and contamination with other sugar chains. However, there are no means to confirm whether the obtained spectrum is correct or not. Although the analysis method is easy and rapid, it lacks accuracy of obtained spectrum and therefore it will not be enough for a means of the structural analysis of sugar chain.

The cause of the above-described defects of this technique resides in lack of identification of each of the reaction product. The term "identification" as used herein means that a substance having an unknown structure is determined to be identical with a substance having a known structure by chromatographic analysis or the like. It is indispensable for the identification to collect all of the possible sugar chains as the standard for the analysis and they should be separated from each other by any analytical method. It is impossible, however, to have a complete collection of all of the possible sugar chains as the standard and to separate and distinguish them from each other because the number of such sugar chains is enormous. For these reasons, the approximation of the experimental spectrum to the theoretical spectrum is employed in place of the identification in this technique.

Fundamentally, however, an indefinite approximation technique should not be employed for the determination of the structure of a substance. So long as the approximation technique is employed, there should be danger that the structure cannot be determined or an incorrect structure is given. Therefore, it has been desired to develop a more exact, reliable, and simple method for determining sugar chain structure.

PROBLEMS TO BE SOLVED BY THE INVENTION

The object of the present invention is to provide a more exact, reliable, and simple method for determining the sugar chain structure, a kit to be used for said method, and novel oligosaccharides useful for said method as standards.

MEANS FOR SOLVING THE PROBLEM

To sum up, the present invention relates to a method for determining the structure of an N-acetyllactosamine type of sugar chain characterized by determining the site of linkage and the mode of linkage of sugar residues at the non-reducing terminal side of a β-N-acetylglucosamine residue linked to an α-mannose residue in M3 core by means of detecting the presence of the β-N-acetylglucosamine residue after enzymatic or chemical treatment of said sugar chain. Further, one of the modes of the method comprises the following steps:

(1) removing β-N-acetylglucosamine residues linked to an α-mannose residue in M3 core selectively, (2) removing the remaining sugar residues at the non-reducing terminal side of a β-N-acetylglucosamine residue linked to an α-mannose residue in M3 core provided that the sugar residues still remain in the sugar chain obtained by step (1), and (3) identifying the resulting products of step (1) or (2) by comparing them with standard sugar chain.

The present invention also relates to a kit for determining the structure of an N-acetyllactosamine type of sugar chain characterized by containing at least one of the oligosaccharides represented by the chemical formula 1:

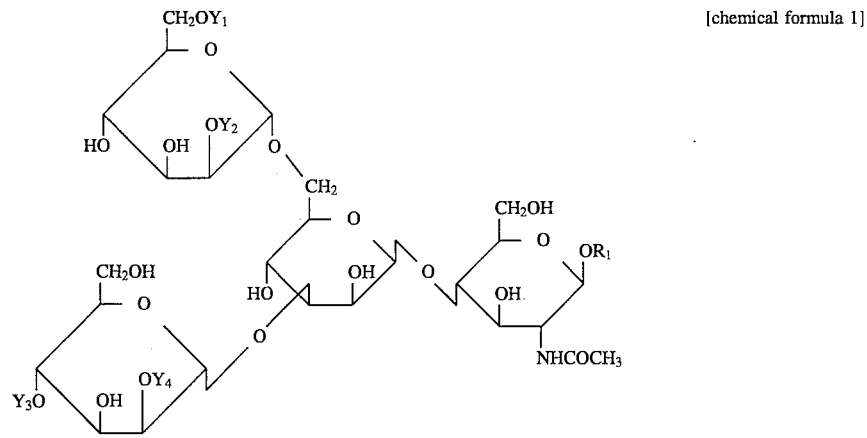

[chemical formula 1]

wherein $Y_1$, $Y_2$, $Y_3$ and $Y_4$ represent hydrogen or a β-N-acetylglucosamine residue, and $R_1$ is represented by the following chemical formula 2 or 3:

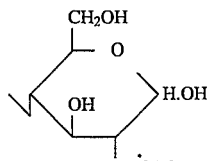
[chemical formula 2]

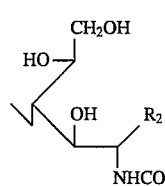
[chemical formula 3]

wherein $R_2$ represents an aldehyde group, a labeled methylene group or a labeled methine group.

The present invention also relates to an oligosaccharide represented by the chemical formula 4:

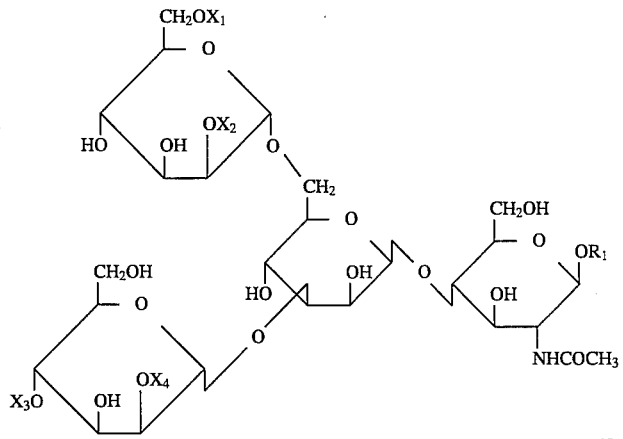
[chemical formula 4]

wherein $X_1$, $X_2$, $X_3$ and $X_4$ represent hydrogen or a β-N-acetylglucosamine residue with the proviso that the case where both $X_1$ and $X_3$ represent hydrogen simultaneously or the case where both $X_2$ and $X_4$ represent β-N-acetylglucosamine residues simultaneously is excepted, and $R_1$, is represented by the chemical formula 2 or 3 above.

The inventors of this invention achieved the purpose of this invention during research into a method of the structural analysis of sugar chains by development of a method of treating a sugar chain in order that the number of the possible products from the treatment should be limited for the sake of the employment of a process of identification, a kit to be used for this method, and novel oligosaccharides useful for a process of identification as standards.

A detailed description will be made on the present invention.

Sugar chains of the N-acetyllactosamine type include, for example, those represented by the following general formula (6).

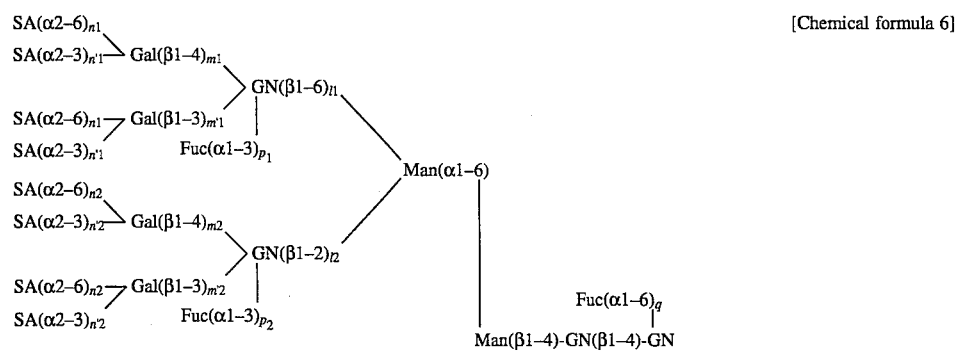
[Chemical formula 6]

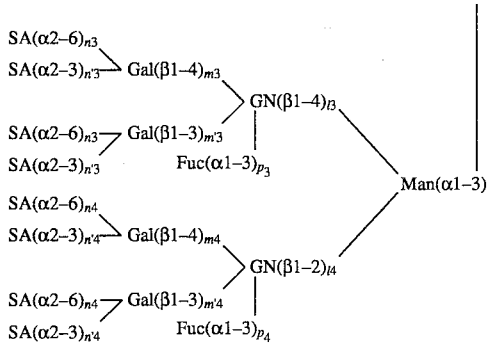

wherein SA represents a sialic acid residue, Gal represents a galactose residue, GN represents an N-acetylglucosamine residue, Fuc represents a fucose residue, Man represents a mannose residue, the symbol in the parentheses following each residue indicates the mode of linkage, and symbols $l_x$, $m_x$, $m'_x$, $n_x$, $n'_x$, and $P_x$ (x being 1, 2, 3 or 4) and q each represent a variable, with the proviso that $m_x m'_x = n_x n'_x = m'_x p_x = 0$ and $l_x \geq m_x, m'_x \geq n_x, n'_x$ and $l_x \geq p_x$.

Although the fine structures of the sugar chains of N-acetyllactosamine type are full of variety, the basic structure thereof has a common structural unit (hereinafter referred to as "M3 core") represented by the following formula (7).

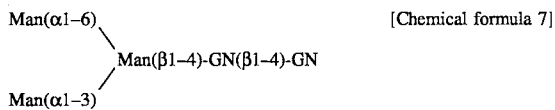
[Chemical formula 7]

All the ordinary structures are represented by the above formula (6). The N-acetyllactosamine type of sugar chain has a dendritic structure comprising the M3 core having branches through four GN's. The branches (hereinafter the group comprising a branched GN and sugar residues at the non-reducing terminal side of the GN will be referred to as "branch") comprise GN, Gal, SA and Fuc sugar residues. Gal and SA each have two modes of linkage, i.e. Galβ-1,3 or Galβ-1,4, and SAα-2,3 or SAα-2,6, respectively. These modes of linkage must be distinguished from each other. The number of each sugar residue constituting a branch is at most 1 and the sequence thereof is fixed. The contents of each branch are represented by the following formula 8.

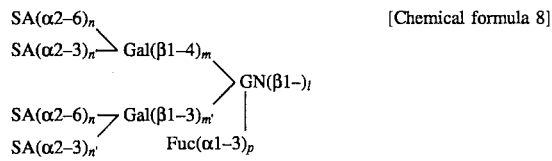
[Chemical formula 8]

Since the number of each sugar residue in a branch is limited to 0 or 1 and the sequence thereof has been specified as the chemical formula 8, the structure of the N-acetyllactosamine type of sugar chain can be determined merely by determining the presence or absence of each sugar residue in each branch, and the sequence of the sugar residues is determined as a matter of course.

The determination of the presence or absence of each sugar residue in each branch is synonymous with the determination of the branch having a certain sugar residue. Therefore, the structure of the N-acetyllactosamine type of sugar chain can be determined by determining the branch having a certain sugar residue in each case.

A description will be made on the technique of determining which branch has a certain sugar residue (branch information).

In a typical mode of the method provided by this invention, the branches having a certain sugar residue of which the presence should be determined, can be distinguished from the branches not having the residue by removing the branches not having the residue from a sugar chain sample by the enzymatic or chemical treatment.

When the branches do not have GN, a sugar chain sample has no branch and thus the removal of the branches not having GN is unnecessary. The branches not having Gal, SA, or Fuc can be removed from a sugar chain sample, for example, in the following way.

When the branches do not have Gal, they may have GN and/or Fuc and thus the branches can be removed, for example, by the treatment of a sugar chain sample with the mixture of two enzymes, β-N-acetylglucosaminidase and α-fucosidase. In the branches having Gal, GN is protected from the treatment by Gal and thus the branches having Gal are not removed. When the branches do not have SA, they may have GN, Gal, and/or Fuc and thus the branches can be removed, for example, by the treatment of a sugar chain sample with the mixture of three enzymes, β-N-acetylglucosaminidase, β-galactosidase, and α-fucosidase. In the branches having SA, GN and Gal are protected from the treatment by SA and thus the branches having SA are not removed. When the branches do not have Fuc, they may have GN, Gal, and/or SA and thus the branches can be removed, for example, by the treatment of a sugar chain sample with the mixture of three enzymes, β-N-acetylglucosaminidase, β-galactosidase, and sialidase. In the branches having Fuc, GN is protected from the treatment by Fuc and thus the branches having Fuc are not removed. After the removal of the branches not having each sugar residue, Gal, SA, and Fuc, according to the method described above, the remaining branches should be identified. For the purpose of the identification, the remaining branches are converted into those with the simplest structure, that is to say the branches having only GN by the enzymatic or chemical treatment. After this treatment, the number of final products is so limited that the final products can be easily identified.

The number of the structures with the M3 core having GN's is calculated as follows: 2×2×2×2=16, because each of the four GN's has two possibilities, i.e. presence and absence. These structures are given in Table 1. The presence or absence of each branch in the treatment product can be determined by identifying the treatment product of the sugar chain with any of the 16 sugar chains, with the proviso that the 16 sugar chains can be separated by any method.

As described above, the branch information for all the sugar residues constituting the branch can be obtained when the treatment can be conducted so as to leave only GN of the branch having a certain sugar residue among the branches and the 16 sugar chains given in Table 1 can be separated and identified by chromatographic analysis or the like. From these data, the structure of the N-acetyllactosamine type of sugar chain represented by the chemical formula 6 can be identified.

Below, a method of the present invention which employs digestion with glycosidases as the treatment of the sugar chain will be explained.

The structure of a typical N-acetyllactosamine type of sugar chain can be principally determined by determining (i) the site of linkage of GN, namely the site of GN linkage (hereinafter the term "the site of linkage of a certain sugar residue" means the branch which has a certain sugar residue and its linkage) (ii) the site and mode of Gal linkage, (iii) the site and mode of SA linkage, and (iv) the site of Fuc linkage.

The following four sites of GN linkage are usually possible in typical sugar chains: GN(β1-6)Man(α1-6), GN(β1-2) Man(α1-6), GN(β1-4)Man(α1-3) and GN(β1-2)Man(α1-3). Determination of the site of GN linkage among these four sites means the determination of the four variables, i.e. $1_1$, $1_2$, $1_3$ and $1_4$, in the formula (6).

The sugar residues to which Gal can be linked are the above-mentioned four GN's, and two modes of Gal linkage, i.e. β-1,3 and β-1,4, are possible. Therefore, the determination of the site and mode of Gal linkage means the determination of the eight variables, $m_1$, $m'_1$, $m_2 m'_2$, $m_3$, $m'_3$, $m_4$ and $m'_4$. Because two or more Gal's are not linked to one GN, $m_x m'_x = 0$ (x being 1, 2, 3 or 4). Further, when $1_x = 0$, then $m_x$, $m'_x = 0$, namely, $1_x \geq m_x$, $m'_x$, because Gal is linked to only GN.

SA can be linked to Gal in two modes of linkage, i.e. α-2,3 and α-2,6. Therefore, the determination of the site and mode of SA linkage means the determination of the eight variables, $n_1$, $n'_1$, $n_2$, $n'_2$, $n_3$, $n'_3$, $n_4$ and $n'_4$ in the above formula (6). Because two or more SA's are not linked to one Gal, $n_x n'_x = 0$ (x being 1, 2, 3 or 4). Further, when $m_x$, $m'_x = 0$, then $n_x, n'_x 0$, namely $m_x$, $m'_x \geq n_x$, $n'_x$, because SA is linked to only Gal.

Fuc can be linked to GN at the reducing terminus of an N-acetyllactosamine type of sugar chain in α-1,6-linkage mode, and also to four GN's in branches in α-1,3-linkage mode. Therefore, the determination of the site and mode of Fuc linkage means the determination of the five variables, q, $p_1$, $p_2$, $p_3$ and $p_4$ in the above formula (6). However, when Gal is linked to GN in β-1,3-linkage mode, it is impossible that Fuc is linked to the GN in α-1,3-linkage mode. Namely, $p_x m'_x = 0$ (x being 1, 2, 3 or 4). Further, when $1_x = 0$, then $p_x = 0$, namely, $p_x \leq 1_x$, since Fuc can be linked to only GN.

The following informations, (i) to (iv), of a certain sugar chain can be determined by digesting the sugar chain with at least one kind of glycosidase and analyzing the reaction products: (i) the site of GN linkage, (ii) the site and mode of Gal linkage, (iii) the site and mode of SA linkage, and (iv) the site of Fuc linkage. In other words, the whole structure of a sugar chain sample can be determined by the enzymatic digestions, which are designed so that only GN linked to M3 core remains; that only GN's at the branches having Gal remain; that only GN's at the branches having SA remain; and that only GN's to which Fuc is linked remain, and by identification of each reaction product by using standard sugar chains.

A description will be made on the standard sugar chains used in the present invention.

The standard sugar chains used in this invention are 16 sugar chains in which only GN's are linked to the M3 core represented by the following formula (9), which include M3 core also.

[Chemical formula 9]

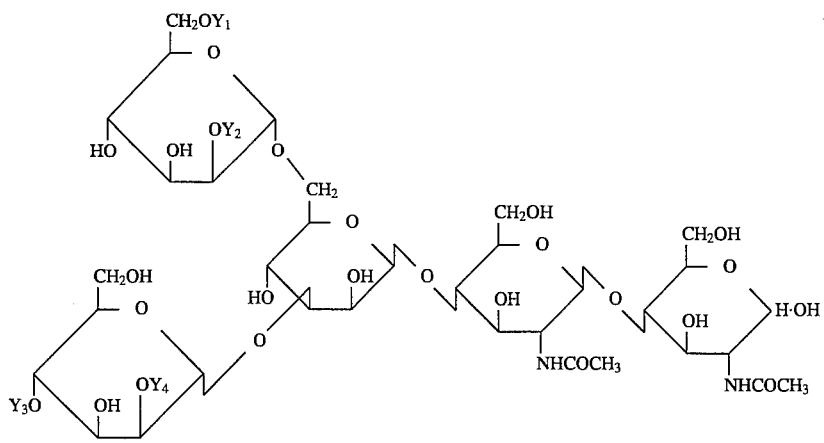

wherein $Y_1$, $Y_2$, $Y_3$ and $Y_4$ each represent hydrogen or β-GN.

By comparing the 16 standard sugar chains with the final reaction products, the site of GN linkage to the M3 core in the final reaction product should be determined. The relationship between 16 sugar chains, namely, oligosaccharides I to XVI, with the site of GN linkage is given in Table 1.

TABLE 1

| oligosaccharides | $Y_1$ | $Y_2$ | $Y_3$ | $Y_4$ |
|---|---|---|---|---|
| I | H | H | β-GN | H |
| II | H | β-GN | β-GN | H |
| III | H | H | β-GN | β-GN |
| IV | H | H | H | H |
| V | H | β-GN | H | H |
| VI | H | H | H | β-GN |
| VII | H | β-GN | H | β-GN |
| VIII | H | β-GN | β-GN | β-GN |
| IX | β-GN | H | H | β-GN |
| X | β-GN | β-GN | β-GN | H |
| XI | β-GN | H | β-GN | β-GN |
| XII | β-GN | H | H | H |
| XIII | β-GN | β-GN | H | H |
| XIV | β-GN | H | β-GN | H |
| XV | β-GN | β-GN | H | β-GN |
| XVI | β-GN | β-GN | β-GN | β-GN |

The oligosaccharides I to XVI can be prepared by digestion with several glycosidases from N-acetyllactosamine type of sugar chain. For example, the oligosaccharide XVI can be prepared by complete digestion of a sugar chain, which can be obtained from human $\alpha_1$-acid glycoprotein (Sigma) by hydrazinolysis and N-acetylation, with sialidase, β-galactosidase, and fucosidase. The oligosaccharide XVI can be partially digested with βN-acetylglucosaminidase from bovine kidney to form a mixture of the oligosaccharides I to XVI, which can be purified by HPLC or the like. Another example is that the oligosaccharide VIII can be prepared by complete digestion of a sugar chain, which can be obtained from bovine fetuin (Sigma) by hydrazinolysis and N-acetylation, with sialidase and β-galactosidase. The oligosaccharide VIII can be partially digested with β-N-acetylglucosaminidase from bovine kidney to form a mixture of the oligosaccharides I to VIII, which can be purified by HPLC or the like. These oligosaccharides can be detected with the pulsed amperometric detector (PAD) with high sensitivity.

These oligosaccharides may be used as intact form or may be used as the form represented by the following formula (10).

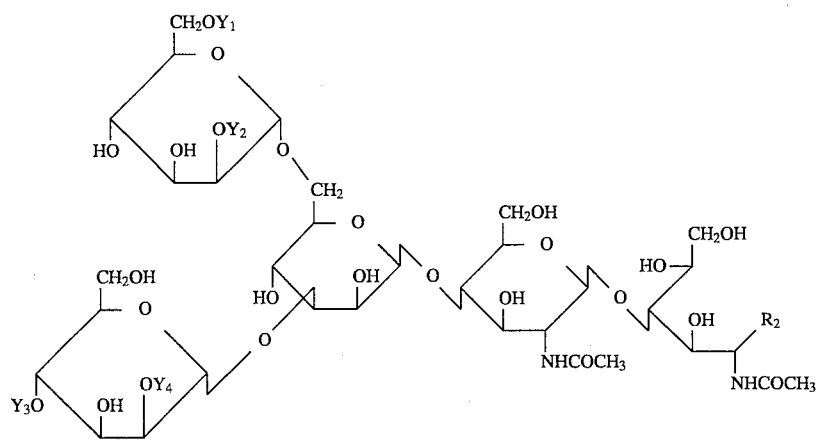

[Chemical formula 10]

wherein $Y_1$, $Y_2$, $Y_3$ and $Y_4$ each represent hydrogen or β-GN, and $R_2$ represents an aldehyde group, a labeled methylene group or a labeled methine group.

The methylene group can be labeled with, for example, 2-aminopyridine [*Agricultural and Biological Chemistry*, 54, 2169–2170 (1990)], p-aminobenzoic acid ethyl ester (ABEE) [*Analytical Biochemistry*, 141, 366–381 (1984)], or 8-aminonaphthalene-1,3,6-trisulfonic acid (ANTS) [*Biochemical Journal*, 270, 705–713 (1990)].

The methine group can be labeled with, for example, radioactive material (tritium) [*Methods in Enzymology*, 50, 50 (1978)] or 1-phenyl-3-methyl-5-pyrazolone (PMP) [*Analytical Biochemistry*, 180, 351–357 (1989)]. Oligosaccharides I to XVI listed in Table 1 may be labeled with 2-aminopyridine. PA-oligosaccharide I to XVI will be referred to as I-PA to XVI-PA, respectively. I-PA to VII-PA can be prepared by, for example, partial digestion of VIII-PA, which can be obtained from oligosaccharide VIII by PA-method, with β-N-acetylglucosaminidase from bovine kidney, and by purification of the digestion products by HPLC. IX-PA to XV-PA can be prepared by, for example, partial digestion of XVI-PA, which can be obtained from oligosaccharide XVI by PA-method, with β-N-acetylglucosaminidase from bovine kidney, and by purification of the digestion products by HPLC. These PA-oligosaccharides can be used as the standard to identify the structure of the final reaction product of this invention.

The mixture of the eight oligosaccharides I-PA to VIII-PA can be separated by, for example, HPLC [eluent: 100 mM acetic acid/triethylamine (pH 4.0 ) containing 0. 035% 1-butanol] with PALPAK TYPE R (Takara Shuzo). FIG. 1 shows an example of the separation of an equimolar mixture of I-PA to VIII-PA. In FIG. 1, the ordinate represents the relative fluorescence intensity and the abscissa represents the elution time (min) (the same shall apply hereinafter).

The mixture of 16 oligosaccharides I-PA to XVI-PA can be separated by HPLC. For example, the mixture is analyzed by HPLC [eluent: 50 mM acetic acid/triethylamine (pH 7.3) containing acetonitrile; linear gradient of acetonitrile 70% (0 min) to 50% (300 min)] with PALPAK TYPE N (Takara Shuzo). I-PA to XVI-PA can be separated from each other on the basis of a difference in the number of the component sugar residues. An example thereof is given in FIG. 2. In FIG. 2, an oligosaccharide in which no GN is linked to the M3 core at all, i.e. IV-PA, is eluted during the period of 13 to 17 min; those in which one GN is linked to the M3 core (I-PA, V-PA, VI-PA and XII-PA) are eluted during the period of 18 to 23 min (fraction 2); those in which two GN's are linked to the M3 core (II-PA, III-PA, VII-PA, IX-PA, XIII-PA and XIV-PA) are eluted during the period of 24 to 29 min (fraction 3); those in which three GN's are linked to the M3 core (VIII-PA, X-PA, XI-PA and XV-PA) are eluted during the period of 32 to 38 min (fraction 4); and that in which four GN's are linked to the M3 core (XVI-PA) is eluted during the period of 42 to 46 min.

When fraction 2 is further purified by HPLC [eluent: 100 mM acetic acid/triethylamine (pH 4.0) containing 0.07% 1-butanol] with PALPAK TYPE R, four oligosaccharides in which one GN is linked (i.e. I-PA, V-PA, VI-PA and XII-PA) can be separated. FIG. 3 shows an example thereof. In the same manner, four oligosaccharides, i.e. VIII-PA, X-PA, XI-PA and XV-PA, can be purified from fraction 4. FIG. 4 shows an example thereof. When fraction 3 is further purified by HPLC [eluent: 100 mM acetic acid/triethylamine containing 0.035% 1-butanol (pH 4.0)] with PALPAK TYPE R, six oligosaccharides, i.e. II-PA, III-PA, VII-PA, IX-PA, XIII-PA and XIV-PA, can be separated. FIG. 5 shows an example thereof. Thus, 16 oligosaccharides, I-PA to XVI-PA, can be separated.

The 16 PA-oligosaccharides can be isolated by pooling the fractions containing each peak in FIGS. 2 to 5. Although XIV-PA can be isolated by pooling the fraction containing the peak in FIG. 5, it can be more easily obtained by the following method. A portion of the fraction 3 can be completely digested with β-N-acetylglucosaminidase from *D. pneumoniae* specific for β-1,2-linkage and then the products can be analyzed by HPLC under the same conditions as those of FIG. 5, and then the peaks of III-PA and VII-PA disappear (because they are converted into I-PA and IV-PA, respectively), leaving only XIV-PA. Thus XIV-PA can be obtained by pooling the fraction containing the remaining peak. An example thereof is given in FIG. 6. IX-PA to XV-PA can also be efficiently prepared from XVI-PA, for example, PA-sugar chain 004 (Takara Shuzo) by use of sialyl transferase and galactose oxidase.

Each of the sixteen PA-oligosaccharides, I-PA to XVI-PA, can be analyzed by HPLC with two kinds of columns, PALPAK TYPE N column [eluent A, a 25:75 mixture of 0.2M acetic acid/triethylamine buffer-at pH 7.3 and acetonitrile; eluent B, a 50:50 mixture of 0.1M acetic acid/ triethylamine buffer at pH 7.3 and acetonitrile; after injection of a sample into the column equilibrated with a 80:20 mixture of eluent A and B, the ratio of eluent B is increased on a linear gradient to 40% over a 75-min period.], and PALPAK TYPE R column [eluent: 100 mM acetic acid/ triethylamine (pH 4.0) containing 0.02% 1-butanol]. A typical elution profiles of the mixture of the sixteen PA-oligosaccharides on the two columns are shown in FIG. 7. The elution position of each PA-oligosaccharide on the two columns can be plotted and thus the two-dimensional sugar map can be made. FIG. 7 also shows an example of two-dimensional sugar map. Final reaction product of this invention can be easily identified by use of this two-dimensional sugar map.

A description will be made on the properties of I-PA, II-PA, III-PA, IX-PA, X-PA, XI-PA, XII-PA, XIII-PA, and XIV-PA. The proton nuclear magnetic resonance ($^1$H-NMR) spectrum of I-PA is given in FIGS. 8 and 9, that of II-PA in FIGS. 10 and 11, that of III-PA in FIGS. 12 and 13, that of IX-PA in FIG. 14, that of X-PA in FIGS. 15 and 16, that of XI-PA in FIG. 17, that of XII-PA in FIG. 18, that of XIII-PA in FIG. 19 and that of XIV-PA in FIG. 20. Chemical shifts are expressed in parts per million from the internal sodium 4,4-dimethyl-4-silapentane-1-sulfonate (DSS) but were actually measured with an internal standard of acetone (2,218 ppm in $D_2O$ at 37° C.). In FIGS. 9, 11, 13, 14, 15, 17, 18, 19 and 20, the signal at 2,218 ppm was that of the methyl proton of acetone used as the internal standard.

(Properties of I-PA)
  Mol. wt. 1192.7 (by mass spectrometry)
  $^1$H-NMR 4,556 (H-1, GN-7), 2,067 (NAc, GN-7)
  Sugar compn. Man: GN=3.0: 2.5, free from Gal and Fuc.
(Properties of II-PA)
  Mol. wt. 1395.4 (by mass spectrometry)
  $^1$H-NMR 4,541 (H-1, GN-5'), 4.556 (H-1, GN-7), 2.040 (NAc, GN-5'), 2.066 (NAc, GN-7)
  Sugar compn. Man: GN=3.0: 3.5, free from Gal and Fuc.
(Properties of III-PA)
  Mol. wt. 1395.5 (by mass spectrometry)
  $^1$H -NMR 4.527 (H-1, GN-5 ), 4.515 (H-1, GN-7 ), 2.045 (NAc, GN-5), 2.067 (NAc, GN-7)
  Sugar compn. Man: GN =3.0: 3.5, free from Gal and Fuc.
(Properties of IX-PA)
  Mol. wt. 1395.0 (by mass spectrometry)
  $^1$H-NMR 4.552 (H-1, GN-7'), 4.535 (H-1, GN-5), 2.046 (NAc, GN-7'), 2.046 (NAc, GN-5)
  Sugar compn. Man: GN=3.0: 3.5, free from Gal and Fuc.
(Properties of X-PA)
  Mol. wt. 1599.0 (by mass spectrometry)
  $^1$H-NMR 4.528 (H-1, GN-7'), 4.549 (H-1, GN-5'), 4.557 (H-1, GN-7), 2,028 (NAc, GN-7'), 2.038 ( NAc, GN- 5'), 2.067 ( NAc, GN- 7 )
  Sugar compn. Man: GN=3.0: 4.5, free from Gal and Fuc.

(Properties of XI-PA)
  Mol. wt. 1598.0 (by mass spectrometry)
  $^1$H-NMR 4.546 (H-1, GN-7'), 4.515 (H-1, GN-7), 4.529 (H-1, GN-5), 2.045 (NAc, GN-7'), 2.065 (NAc, GN-7), 2.045 (NAc, GN-5)
  Sugar compn. Man: GN=3.0: 4.5, free from Gal and Fuc.
(Properties of XII-PA)
  Mol. wt. 1191.5 (by mass spectrometry)
  $^1$H-NMR 4,542 (H-1, GN-7'), 2.043 (NAc, GN-7')
  Sugar compn. Man: GN=3.0: 2.5, free from Gal and Fuc.
(Properties of XIII-PA)
  Mol. wt. 1395.0 (by mass spectrometry)
  $^1$H-NMR 4,530 (H-1, GN-7'), 4.548 (H-1, GN-5'), 2,027 (NAc, GN-7'), 2.038 (NAc, GN-5')
  Sugar compn. Man: GN=3.0: 3.5, free from Gal and Fuc.
(Properties of XIV-PA)
  Mol. wt. 1395.0 (by mass spectrometry)
  $^1$H-NMR 4.545 (H-1, GN-7'), 4.556 (H-1, GN-7), 2.043 ( NAc, GN- 7'), 2.065 ( NAc, GN- 7 )
  Sugar compn. Man: GN=3.0: 3.5, free from Gal and Fuc.

The reference numerals of the sugar residues in the $^1$H-NMR spectra are as shown in the following chemical formula (11):

[Chemical formula 11]

$$\begin{array}{c} ^7GN(\beta1-6) \\ \phantom{xxxxxxxx} \searrow ^{4'} \\ ^{5'}GN(\beta1-2)-Man(\alpha1-6) \\ \phantom{xxxxxxxxxxxxxxxxxxx} \searrow ^3 \phantom{xx} ^2 \phantom{xx} ^1 \\ \phantom{xxxxxxxxxxxxxxxxxxxxxxxx} Man(\beta1-4)GN(\beta1-4)GN \\ \phantom{xxxxxxxxxxxxxxxxxxx} \nearrow ^4 \\ ^7GN(\beta1-4)-Man(\alpha1-3) \\ \phantom{xxxx} \nearrow \\ ^5GN(\beta1-2) \end{array}$$

When the enzymatic digestion is employed as the treatment in the method of the present invention, a sugar chain sample is digested with glycosidases in one or more steps including a reaction-termination operation in the course of the reaction, and the final product is subjected to chromatographic analysis comparing with the above-described standard sugar chains.

The sugar chain to be analyzed may be any of those represented by above chemical formula (6). Even a sugar chain which is not represented by the formula (6) can be analyzed by the method of the present invention so far as it can be converted into that represented by the formula (6) by enzymatic or chemical treatments.

For example, a sugar chain with a polylactosamine structure, which has the repeating N-acetyllactosamine [(-3)Gal($\beta$1-4)GlcNAc($\beta$1-)] being linked to the Gal residues of the formula (6) is not represented by the formula (6). The sugar chain with polylactosamine can be converted into a sugar chain represented by the formula (6) by sequential digestion with $\beta$-galactosidase and $\beta$-N-acetylglucosaminidase [T. Ohkura et al., *J. Biol. Chem.* (1981) 256, 8485–8490] or by digestion with endo-$\beta$-galactosidase from *Escherichia freundii*.

The sugar chain to be analyzed may be labeled or not. Although the sugar chain sample may be a mixture of several sugar chains, the purity thereof is preferably at least 80%.

The glycosidase used in the respective steps may be a single one or a mixture of two or more glycosidases. Although the glycosidase to be used is preferably exoglycosidases, endoglycosidases can also be used. The reaction temperature which may not be particularly limited is usually 20 to 50° C. preferably 37° C. The reaction time which may not be particularly limited is usually 10 min to 20 h, preferably 3 to 5 h. After each step, the reaction is terminated by inactivation of the glycosidases by incubating the reaction mixture at 80° to 120° C. for 3 to 10 min. Such an inactivation step is not always necessary. In other words, the inactivation step is not always necessary when the glycosidases used in the previous step show no activities because the optimum temperature, pressure, pH, concentration of the organic solvent, etc., of the subsequent step are extremely different from those of the previous step, or when the glycosidase used in the previous step can be removed with antibody beads or an ion-exchange resin.

The analytical method of the reaction product, which may not be particularly limited, may include thin layer chromatography, electrophoresis, mass spectrometry, gas chromatography, etc., and the analysis by HPLC is preferable. The reaction sequence usually includes 1 to 6 reactions per sample. The products of each reaction are analyzed, and the sugar chain structure is determined by combining various pieces of the information thus obtained. Below, each reaction is described in detail.

(i) Determination of the site of GN linkage

When a sugar chain sample is digested with a mixture of β-galactosidase, sialidase, and α-fucosidase, Gal, SA, and Fuc can be removed from the chain, leaving GN. Therefore, the reaction product should be one of sugar chains repesented by chemical formula (9) or (10). The reaction product can be identified by using the above-described standard sugar chains, and then the site of GN linkage in the starting sugar chain sample, i.e. the variables $1_1$, $1_2$, $1_3$ and $1_4$ in the formula (6), can be determined. The glycosidases used herein can be preferably those having a low substrate specificity, such as β-galactosidase from jack beans (Seikagaku-Kogyo), β-galactosidase from Streptococcus (Seikagaku-Kogyo), sialidase from *Arthrobacter ureafaciens* (Nacalai Tesque), α-fucosidase from bovine kidney (Boehringer Mannheim), etc.

(ii) Determination of the site and mode of Gal linkage

When a sugar chain sample is digested with a mixture of β-N-acetylglucosaminidase, sialidase, and α-fucosidase, Fuc and GN, which is not substituted by Gal, can be removed from the chain, leaving Gal and GN at the same branch. After removal or inactivation the enzymes, the sugar chain is further digested with β-galactosidase to remove Gal. The reaction product must be one of sugar chains repesented by chemical formula (9) or (10). The reaction product can be identified by using the above-described standard sugar chains, and then the site of Gal linkage in the starting sugar chain sample can be determined. By this reaction, the mode of Gal linkage cannot be determined. Namely, it can be determined only that either $m_x$ or $m'_x$ (x being 1, 2, 3 or 4) is 1 or, in other words, it can be determined that $(m_x+m'_x)$ is either 0 or 1. The glycosidases used herein can be preferably those having a low substrate specificity, such as β-N-acetylglucosaminidase from bovine kidney (Boehringer Mannheim), β-galactosidase from jack beans, β-galactosidase from Streptococcus, sialidase from *A. ureafaciens,* and α-fucosidase from bovine kidney.

To determine the mode of Gal linkage, a sugar chain sample is digested with the same mixture of glycosidases as described above except that a linkage-specific β-galactosidase is used. The sugar chain is digested with a mixture of β-N-acetylglucosaminidase, sialidase, α-fucosidase and β-1, 4-linkage specific or β-1,3-linkage-specific β-galactosidase. Gal, which can be digested with the linkage-specific β-galactosidase, and GN at the same branch, and Fuc and GN, which are not substituted by Gal, can be removed from the chain, leaving Gal, which cannot be digested with the linkage-specific β-galactosidase, and GN at the same branch. After removal or inactivation of the enzymes, the sugar chain is further digested with non-specific β-galactosidase to remove Gal. The reaction product must be one of sugar chains repesented by chemical formula (9) or (10). The reaction product can be identified by using the above-described standard sugar chains, and then the site of Gal linkage, which cannot be hydrolyzed with the linkage specific β-galactosidase, in the starting sugar chain sample can be determined. For example, when β-1,4-linkage specific β-galactosidase from *D. pneumoniae* (Boehringer Mannheim) is used, the site of Galβ-1,3-linkage, i.e. the variables $m'_1$, $m'_2$, $m'_3$ and $m'_4$ in the formula (6), can be determined. Because $m_1+m'_1$, $m_2+m'_2$, $m_3+m'_3$ and $m_4+m'_4$ have been determined by the above-described reaction, the site of Galβ-1,4-linkage, namely, the variables $m_1$, $m_2$, $m_3$ and $m_4$ in the formula (6), can be determined by combining these data.

(iii) Determination of the site and mode of SA linkage

When a sugar chain sample is digested with a mixture of β-N-acetylglucosaminidase, β-galactosidase, and α-fucosidase, Gal and GN, which are not substituted by SA, can be removed from the chain, leaving SA, Gal, and GN at the same branch. After removal or inactivation of the enzymes, the sugar chain is further digested with the mixture of sialidase and β-galactosidase. The reaction product must be one of sugar chains repesented by chemical formula (9 ) or (10 ). The reaction product can be identified by using the above-described standard sugar chains, and then the site of SA linkage in the starting sugar chain sample can be determined. By this reaction, the mode of SA linkage cannot be determined. Namely, it is determined only that either $n_x$ or $n'_x$ (x being 1, 2, 3 or 4) is 1 or, in other words, it is determined that $(n_x+n'_x)$ is either 0 or 1. The glycosidases used herein can be preferably those having a low substrate specificity, such as β-N-acetylglucosaminidase from bovine kidney, β-galactosidase from jack beans, β-galactosidase from Streptococcus, sialidase from *A. ureafaciens*, α-fucosidase from bovine kidney, etc.

To determine the mode of SA linkage, a sugar chain sample is digested with the same mixture of glycosidases as described above except that a linkage-specific sialidase is used. The sugar chain is digested with a mixture of β-N-acetylglucosaminidase, β-galactosidase, α-fucosidase and α-2,3-linkage- or α-2,6-linkage-specific sialidase. SA, which cannot be hydrolyzed with the specific sialidase used in the reaction, and Gal and GN at the same branch are left after the reaction. After removal or inactivation of the enzymes, the sugar chain is further digested with non-specific sialidase and β-galactosidase to remove SA and Gal. The reaction product must be one of the sugar chains represented by chemical formula (9) or (10). The reaction product can be identified by using the above-described standard sugar chains, and then the site of SA linkage, which cannot be hydrolyzed with the linkage specific sialidase, in the starting sugar chain sample can be determined. For example, when α-2,3-linkage-specific sialidase from *Salmonella typhimurium* (Takara Shuzo) is used, the site of SAα-2,6-linkage by this reaction, i.e. the variables $n_1$, $n_2$, $n_3$ and $n_4$ in the formula (6) can be determined. Since $n_1+n'_1$, $n_2+n'_2$, $n_3+n'_3$ and $n_4+n'_4$ have been determined by the above-described reaction, the site of SAα-2,3-linkage, namely, the variables $n'_1$, $n'_2$, $n'_3$ and $n'_4$ in the formula (6), can be determined by combining these data.

When only the site and the mode of SA linkage in a sugar chain sample should be determined, the standard oligosaccharides represented by the formula (9) or (10) are not necessarily used. For example, when the site and the mode of SA linkage in the so-called biantennary sugar chain, i.e.

the variables, $n_2$, $n'_2$, $n_4$, and $n'_4$ in the formula (6) should be determined, the sugar chain sample is digested with β-galactosidase first, and then the enzyme is removed or inactivated. Then the reaction mixture is digested with sialidase. After the enzymatic digestion, Gal that is linked by SA must remain and thus the reaction product must be one of the four kinds of product that is to say the oligosaccharides represented by the formula (6) with the variables, ($1_2=1_4=1$, $m_2=m_4=0$), ($1_2=1_4=1$, $m_2=0$, $m_4=1$), ($1_2=1_4=1$, $m_2=1$, $m_4=0$), and ($1_2=1_4=1$, $m_2=m_4=1$). Therefore if the reaction product is identified with these four standard oligosacchrides, the site of SA linkage can be determined, and also, the mode of SA linkage can be determined by use of a sialidase that is specific for α-2,3-linkage.

(iv) Determination of the site of Fuc linkage

When a sugar chain sample is digested with a mixture of β-N-acetylglucosaminidase, β-galactosidase, and sialidase, Fuc and GN substituted by Fuc are left, while other GN, Gal and SA are removed from the chain. After removal or inactivation of the enzymes, the sugar chain is further digested with α-fucosidase to remove Fuc. If necessary, β-galactosidase is also added in the mixture, because Gal which is linked to the same GN as Fuc is linked may remain after the above-described reaction. The reaction product must be one of the sugar chains represented by chemical formula (9) or (10). The reaction product can be identified by using the above-described standard sugar chains, and then the site of Fucα-1,3-linkage in the starting sugar chain sample, i.e., the variables $p_1$, $P_2$, $P_3$ and $P_4$ in the formula (6), can be determined. The glycosidase used herein can be preferably one having a low substrate specificity, such as kβ-N-acetylgluocosaminidase from bovine kidney, β-galactosidase from jack beans, β-galactosidase from Streptococcus, sialidase from A. ureafaciens, α-fucosidase from bovine kidney, etc.

The presence or absence of Fucα-1,6-linkage to GN at the reducing terminus of the sugar chain sample, namely, the variable q, in the formula (6) can be determined by using α-1,3/4-linkage-specific α-fucosidase. When the sugar chain is digested with a mixture of β-N-acetylglucosaminidase, β-galactosidase, sialidase and, for example, α-1,3/4-fucosidase from Streptomyces (Takara Shuzo), GN, Gal, SA and α-1,3-linked Fuc are removed, leaving α-1,6-linked Fuc. Thus, when the sugar chain sample is free from α-1,6-linked Fuc or, in other words, when q is 0, the product must be the M3 core, which can be distinguished from M3 core with α-1,6-linked Fuc. From these results, the presence or absence of Fucα-1,6-linkage can be determined.

The N-acetyllactosamine type of sugar chain occasionally contains Fuc(α1-2)Gal sequence, in addition to the modes of linkage represented by the formula (6). The site of Fucα-1,2-linkage can be determined by the same reaction as described above except that an α-1,2-linkage-specific fucosidase, such as α-1,2-fucosidase from Arthrobacter (Takara Shuzo), is used.

(v) Determination of structure of sugar chain

When the structure of the sugar chain sample to be analyzed is represented by the formula (6), the definite structure can be determined from the above-described results, (i) to (iv). The site of GN linkage, namely, the variables, $1_1$, $1_2$, $1_3$ and $1_4$ in the formula (6), can be determined from the results of (i); the site and mode of Gal linkage, namely, the variables, $m_1$, $m'_1$, $m_2$, $m'_2$, $m_3$, $m'_3$, $m_4$ and $m'_4$ in the formula (6), can be determined from the results of (ii); the site and mode of SA linkage, namely, the variables $n_1$, $n'_1$, $n_2$, $n'_2$, $n_3$, $n'_3$, $n_4$ and $n'_4$ in the formula (6), can be determined from the results of (iii); and the site of Fuc linkage, namely, the variables q, $p_1$, $p_2$, $p_3$ and $p_4$ in the formula (6), can be determined from the results of (iv).

In another mode of the method provided by this invention, the branches having a certain sugar residue of which the presence should be determined, can be distinguished from the branches not having the residue by removing the branches having the residue from a sugar chain sample by the enzymatic or chemical treatment. For example, GN residues in the branches having Galβ-1,3-linkage can be specifically removed by digestion with lacto-N-biosidase, which releases disaccharide, Gal(β1-3)GN, from the non-reducing terminus of a sugar chain [M. Sano et al., Proc. Natl. Acad. Sci. U.S.A.89, 8512–8516 (1992)]. The branches having Gal(β1-3)GN can be specifically removed by the treatment with the mixture of sialidase, α-fucosidase, and lacto-N-biosidase. Then the reaction products can be digested with β-galactosidase and the final reaction product must be one of sugar chains represented by chemical formula (9) or (10). The branches being missing from the branches having GN by this treatment can be determined as the branches having Gal(β1-3)GN, i.e. the branches having Galβ-1,3-linkage.

The usefulness of the method of the present invention for determining the structure of the sugar chain can be further improved by using oligosaccharides represented by the following formula (12), as the standard sugar chains.

[Chemical formula 12]

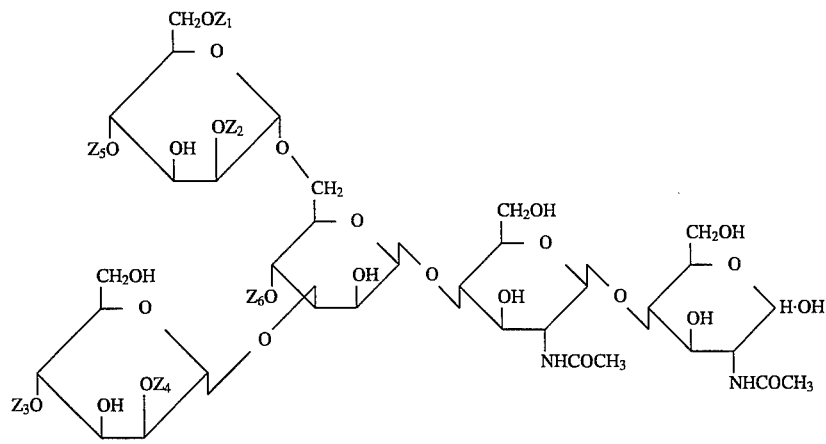

wherein $Z_1$, $Z_2$, $Z_3$, $Z_4$, $Z_5$ and $Z_6$ each represent hydrogen or β-GN.

Though most of the N-acetyllactosamine type of sugar chains are represented by the formula (6), some sugar chain; have the core structure represented by the above formula (12), which can be modified with Gal, SA and Fuc residues. The standard sugar chains represented by formula (12) might be useful for the analysis of these sugar chains. Five oligosaccharides which are particularly useful for the analysis are given in Table 2.

TABLE 2

| oligo-saccharides | $Z_1$ | $Z_2$ | $Z_3$ | $Z_4$ | $Z_5$ | $Z_6$ |
|---|---|---|---|---|---|---|
| XVII | H | β-GN | H | β-GN | H | β-GN |
| XVIII | H | β-GN | β-GN | β-GN | H | β-GN |
| XIX | β-GN | β-GN | H | β-GN | H | β-GN |
| XX | β-GN | β-GN | β-GN | β-GN | H | β-GN |
| XXI | β-GN | β-GN | β-GN | β-GN | β-GN | β-GN |

These oligosaccarides can be used without labeling or after labeling like the oligosaccharides I to XVI.

The typical mode of a method of the present invention includes a process of identifying the resulting product from the treatment by comparing with the standard sugar chains, however, if the structure of the resulting product can be determined by other analytical techniques including NMR spectroscopy and mass spectrometry, these can be employed for the present invention.

The structure of the sugar chain can be determined more easily by combining reagents used in the process of the present invention to form a kit. The kit comprises at least one of the oligosaccharides of the formula (1) and, if necessary, another oligosaccharide of the formula (9) or (10). For example, a kit containing I-PA to VIII-PA is effective particularly in analyzing a biantennary sugar of the formula (6) wherein $1_1=1_3=0$ and $1_2=1_4=1$, or a triantennary sugar of the same formula (6) wherein $1_1=0$ and $1_2=1_3=1_4=1$. For example, a kit containing I-PA to XVI-PA is widely usable for the analysis of the N-acetyllactosamine type of sugar chains.

The kit may contain glycosidases, a column for the analysis, buffer solution, etc., in addition to the oligosaccharide. The reagents to be contained in the kit may be in the form of either a solution or freeze-dried product.

BRIEF DESCRIPTION OF THE DRAWINGS

FIG. 3 shows a chart obtained by HPLC of fraction 2 in FIG. 2 under the Condition 3.

FIG. 4 shows a chart obtained by HPLC of fraction 4 in FIG. 2 under the Condition 3.

EXAMPLES

The following Examples will further illustrate the present invention, which by no means limit the invention.

EXAMPLE 1

200 nmol of commercially available oligosaccharide VIII-PA (PA Sugar Chain 013; Takara Shuzo) was digested with 20 mU of β-N-acetylglucosaminidase from D. pneumoniae (Boehringer Mannheim) in 50 mM phosphate/citrate buffer (pH 5.0) at 37° C. A part of the reaction mixture was analyzed by HPLC, and when the nondegraded substance had amounted to about 25% of the whole, the reaction mixture was treated at 100° C. for 5 min to terminate the reaction. Then the products were separated treated by HPLC to obtain I-PA (22.4 min), II-PA (42.5 min) and III-PA (25.2 min), which were then purified. The HPLC conditions were as follows:

apparatus: LC 6A (Shimadzu), column: PALPAK TYPE R (4.6 mmφ×250 mm) (Takara Shuzo)

eluent: 100 mM acetic acid/triethylamine containing 0.035% of 1-butanol (pH 4.0)

detection: conducted with fluorescence detector RF-535 (Shimadzu) at excitation wavelength of 320 nm and fluorescence wavelength of 400 nm flow rate: 1 ml/min column temperature: 40° C.

(hereinafter referred to as "Condition 1")

Then the composition of each of three purified oligosaccharides, I-PA, II-PA and III-PA, were analyzed by mass spectrometry with a API-III mass spectrograph (Perkin-Elmer Sciex), NMR spectroscopy (in $D_2O$) with a 400 MHz proton nuclear magnetic resonance spectrometer (Bruker), and monosaccharide analysis after acid hydrolysis.

Figure 8:
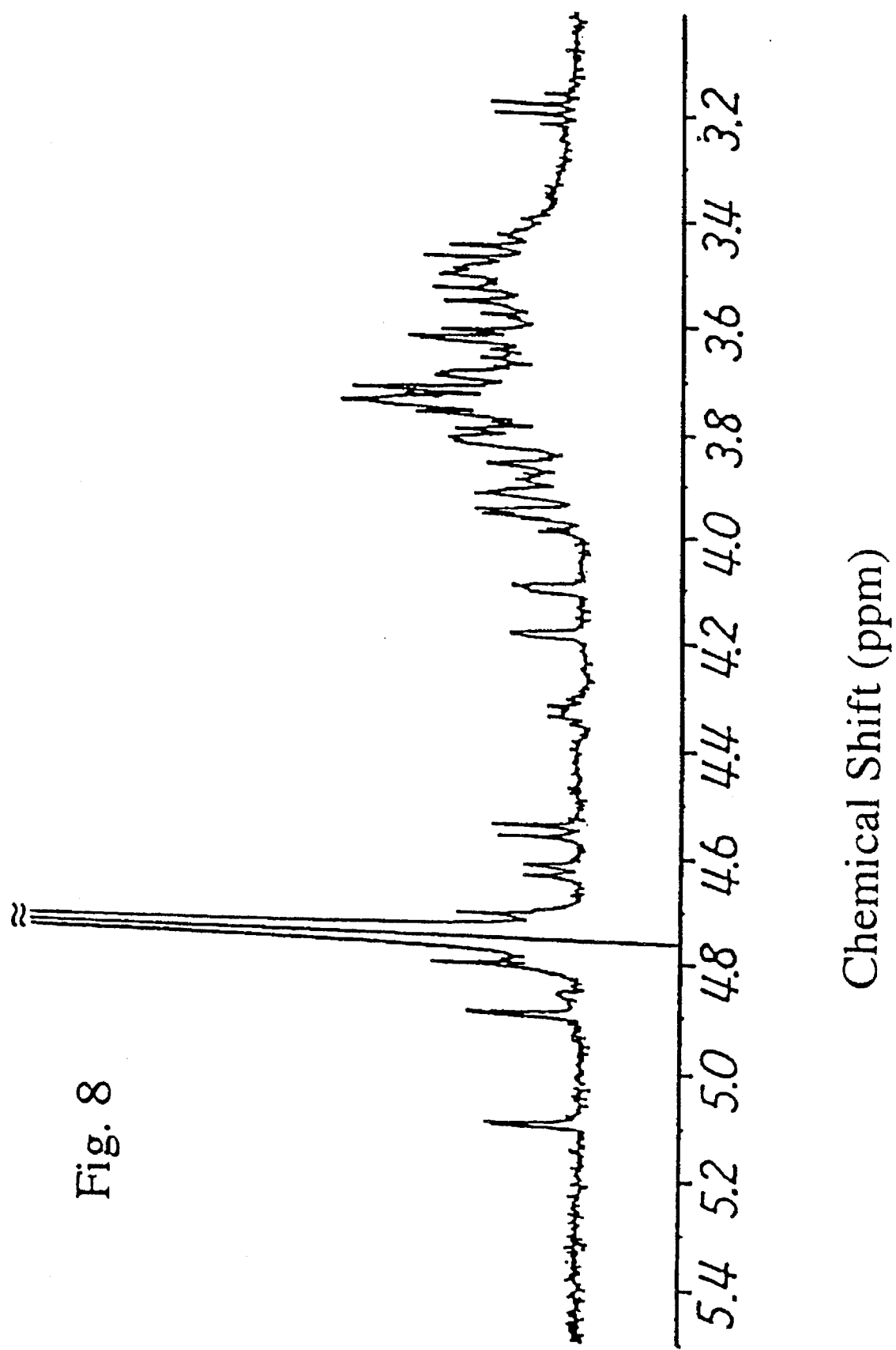
FIG. 8 shows the $^1$H-NMR spectrum, in the range of chemical shift of 3.00 to 5.50 ppm, of I-PA.
Figure 9:
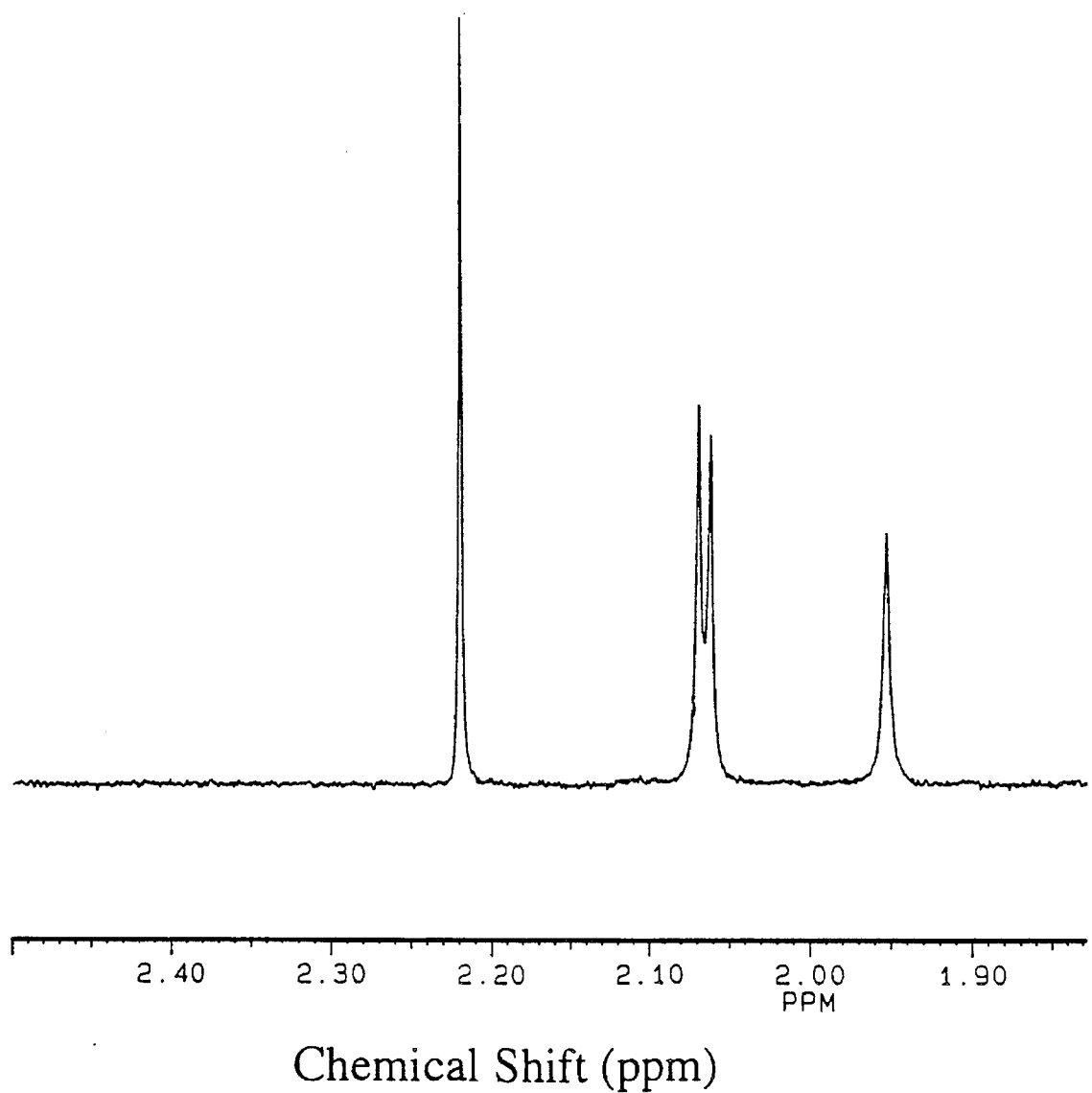
FIG. 9 shows the $^1$H-NMR spectrum, in the range of chemical shift of 1.85 to 2.50 ppm, of I-PA.
Figure 10:
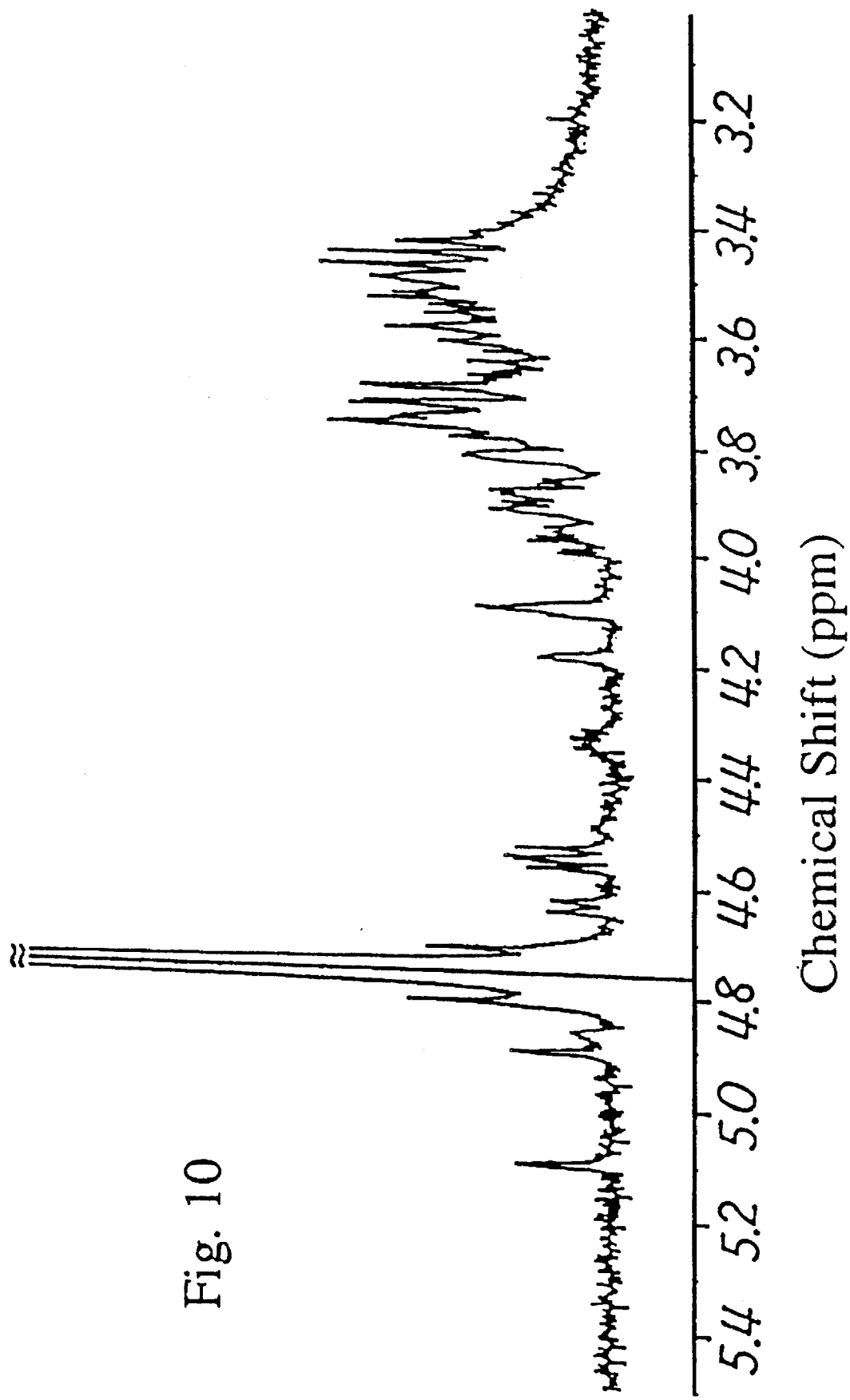
FIG. 10 shows the $^1$H-NMR spectrum, in the range of chemical shift of 3.00 to 5.50 ppm, of II-PA.
Figure 11:
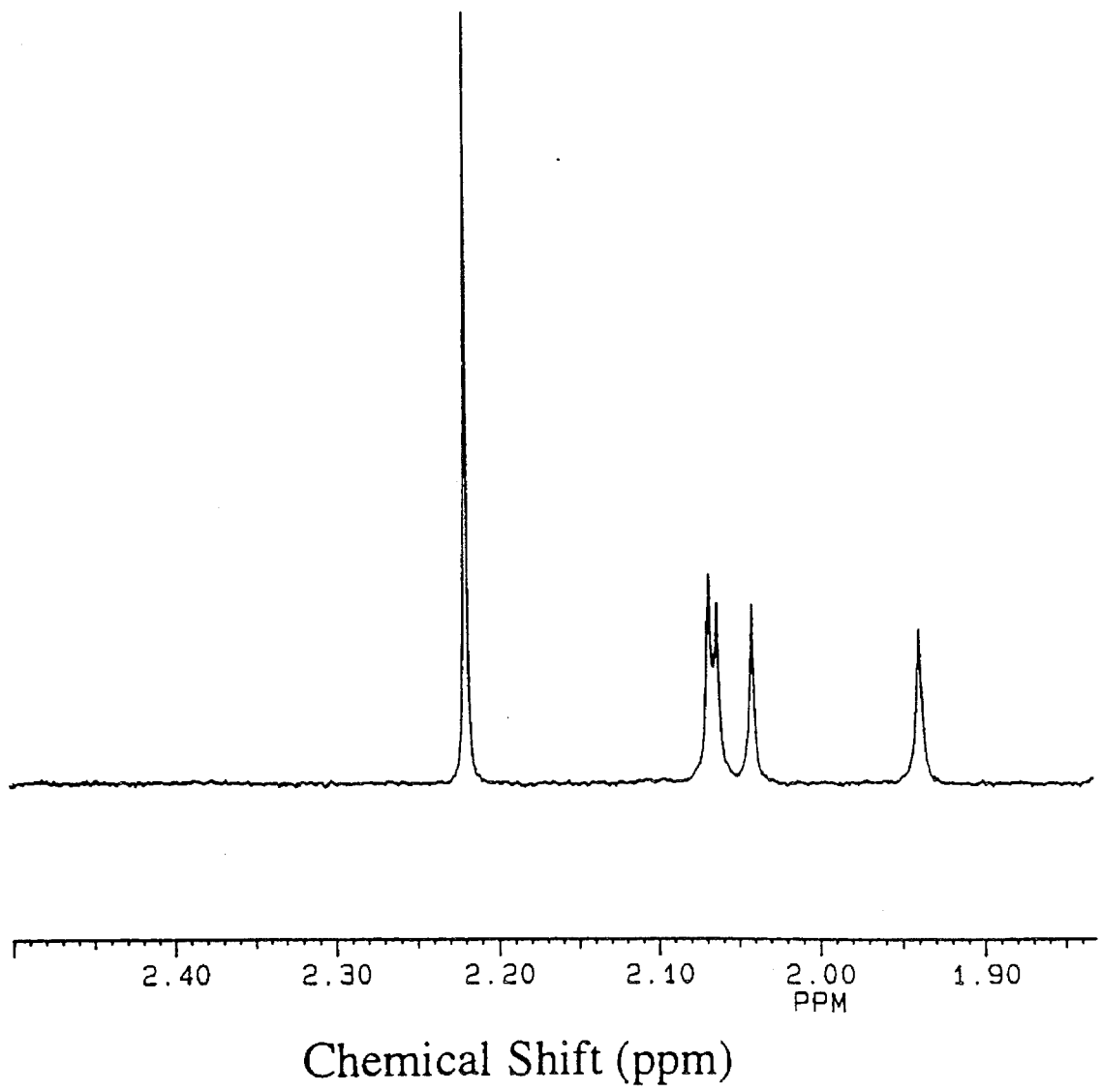
FIG. 11 shows the $^1$H-NMR spectrum, in the range of chemical shift of 1.85 to 2.50 ppm, of II-PA.
Figure 12:
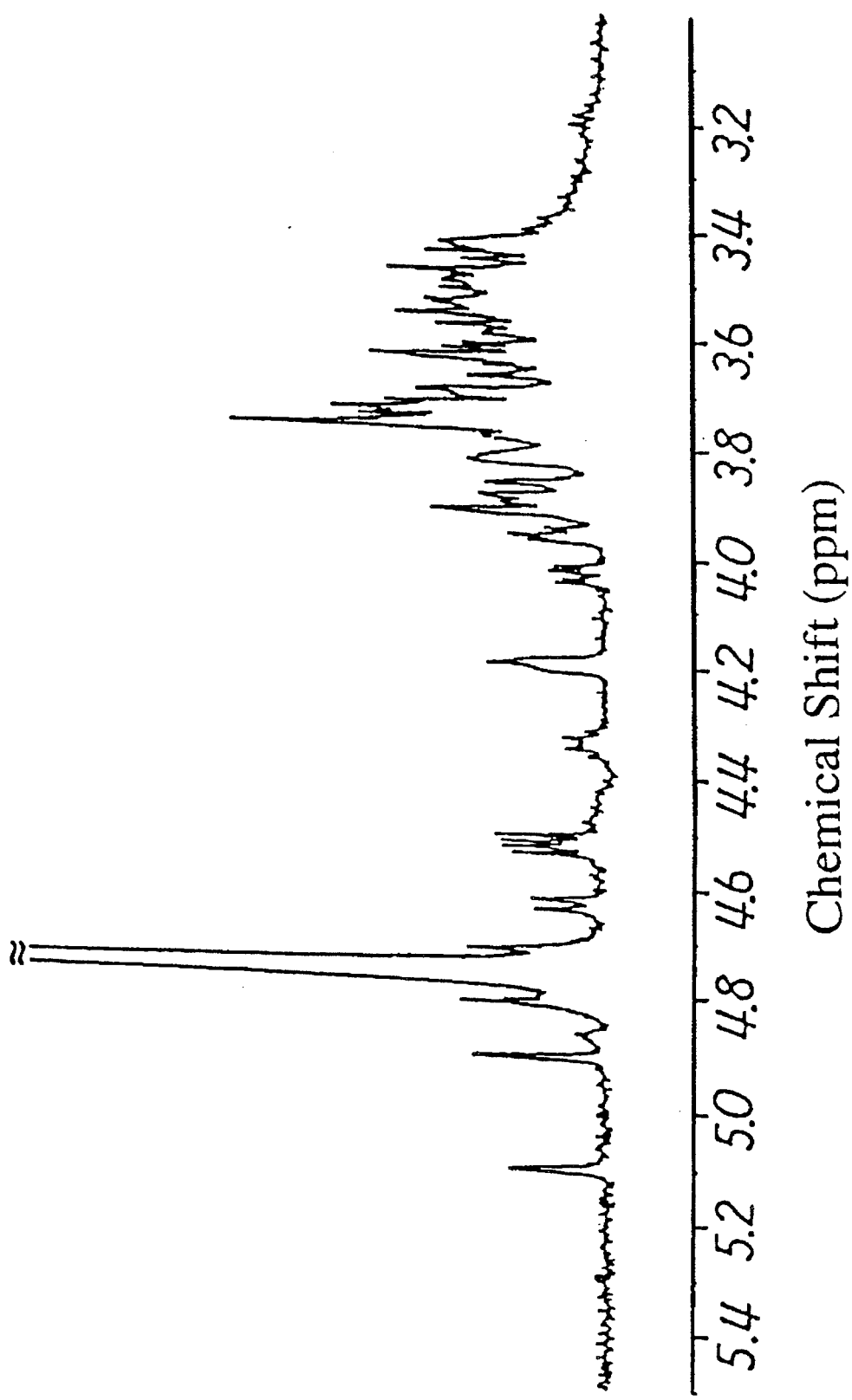
FIG. 12 shows the $^1$H-NMR spectrum, in the range of chemical shift of 3.00 to 5.50 ppm, of III-PA.
Figure 13:
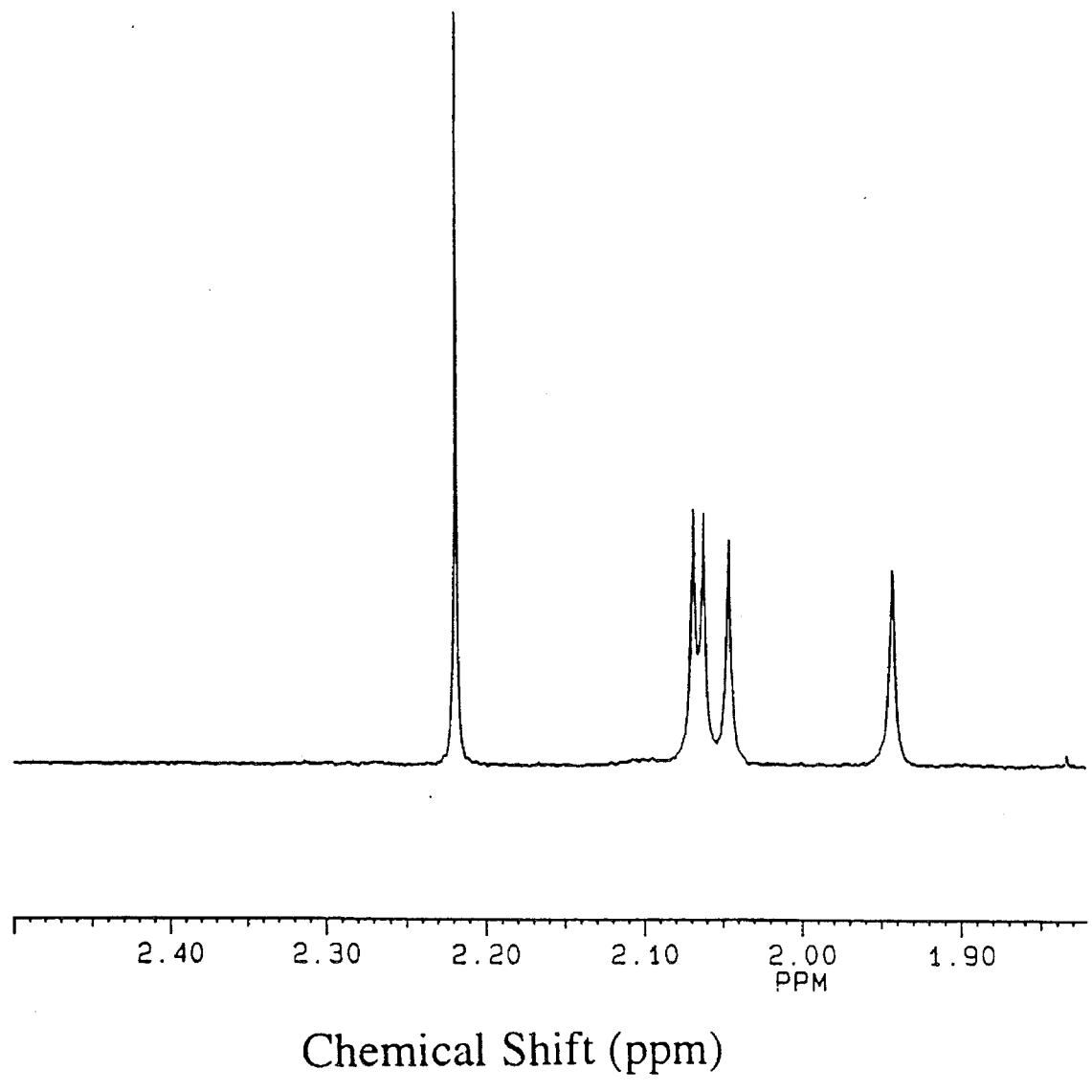
FIG. 13 shows the $^1$H-MNR spectrum, in the range of chemical shift of 1.85 to 2.50 ppm, of III-PA.
Figure 14:
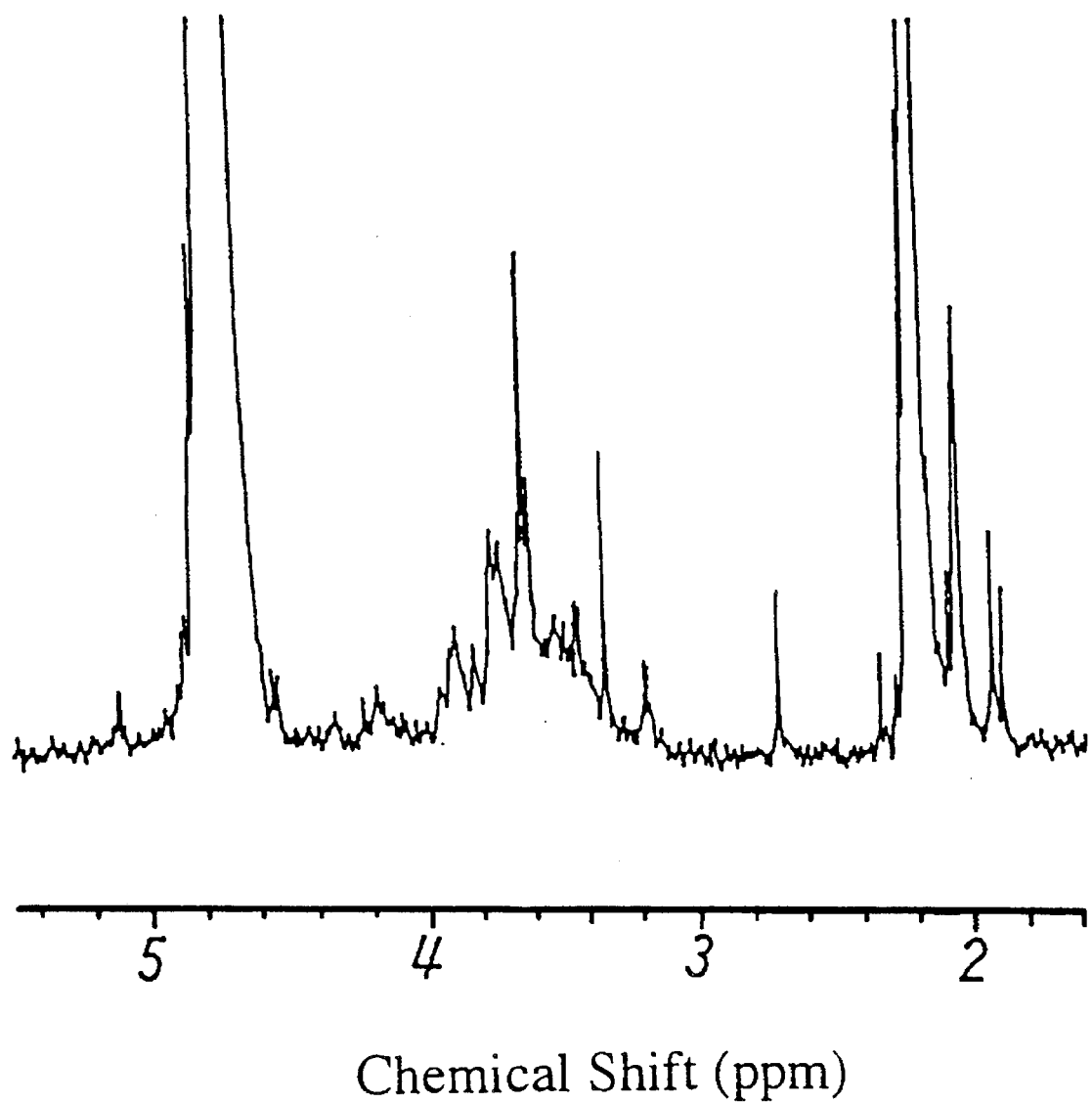
FIG. 14 shows the $^1$H-MNR spectrum, in the range of chemical shift of 1.60 to 2.50 ppm, of IX-PA.
Figure 15:
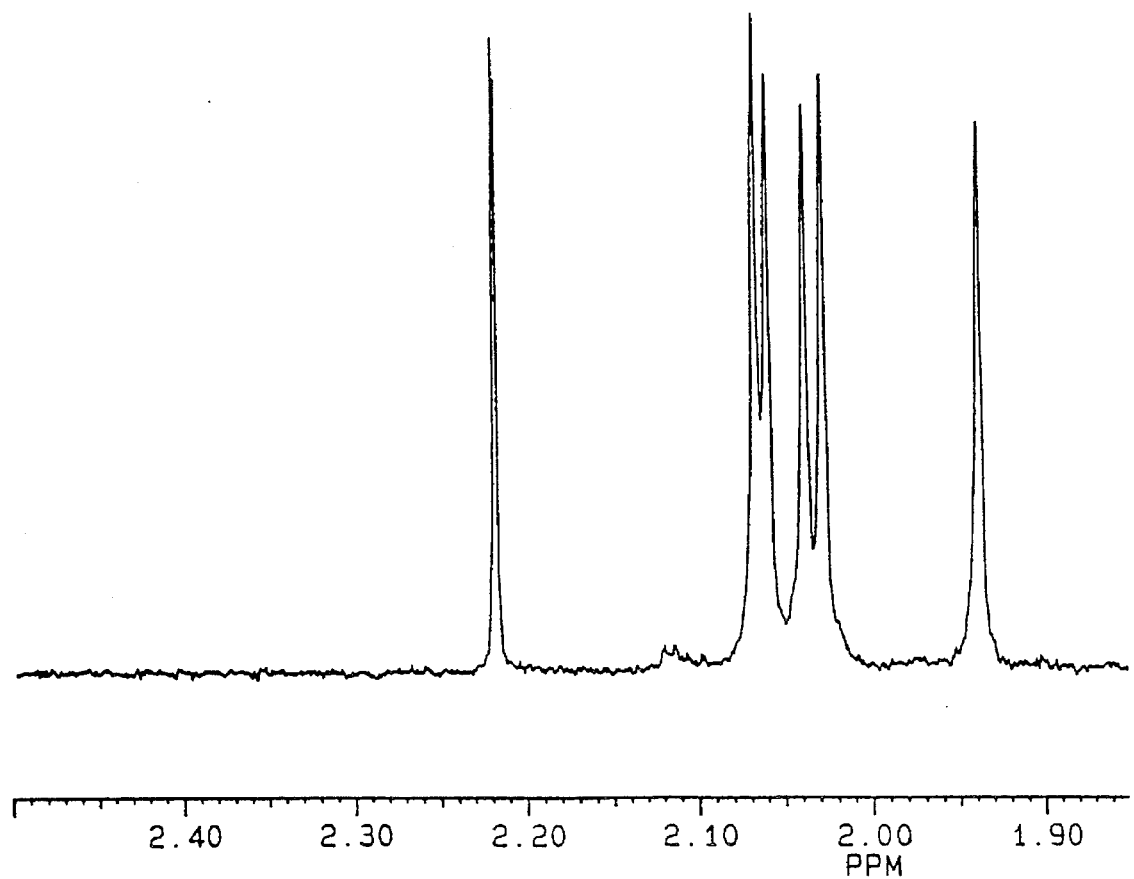
FIG. 15 shows the $^1$H-MNR spectrum, in the range of chemical shift of 1.85 to 2.50 ppm, of X-PA.

The properties of the respective oligosaccharides are given below. Further, the $^1$H-NMR spectrum of I-PA is given in FIGS. 8 and 9, that of II-PA in FIGS. 10 and 11 and that of III-PA in FIGS. 12 and 13. The chemical shift values in these $^1$H-NMR spectra are represented by taking the chemical shift value of the methyl proton of acetone in $D_2O$ at 37° C. as 2.218 ppm when DSS is used as the standard. In FIGS. 9, 11 and 13, the signal at 2.218 ppm was that of the methyl proton of acetone used as the internal standard.

(Properties of I-PA)

Mol. wt. 1192.7

$^1$H-NMR 4.556 (H-1, GN-7), 2.067 (NAc, GN-7)

Sugar compn. Man: GN=3.0: 2.5, free from Gal and Fuc.

(Properties of II-PA)

Mol. wt. 1395.4

$^1$H-NMR 4.541 (H-1, GN-5'), 4.556 (H-1, GN-7), 2.040 (NAc, GN-5'), 2.066 (NAc, GN-7)

Sugar compn. Man: GN=3.0: 3.5, free from Gal and Fuc.

(Properties of III-PA)

Mol. wt. 1395.5

$^1$H-NMR 4.527 (H-1, GN-5), 4.515 (H-1, GN-7), 2.045 (NAc, GN-5), 2,067 (NAc, GN-7)

Sugar compn. Man:GN=3.0: 3.5, free from Gal and Fuc.

The reference numerals of the sugar residues in the $^1$H-NMR spectra are as shown in the following chemical formula (11):

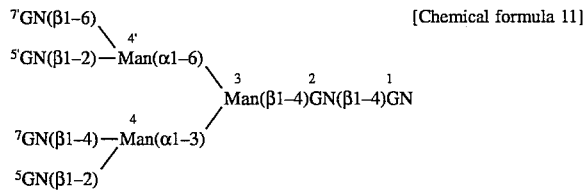

[Chemical formula 11]

EXAMPLE 2

Figure 1:
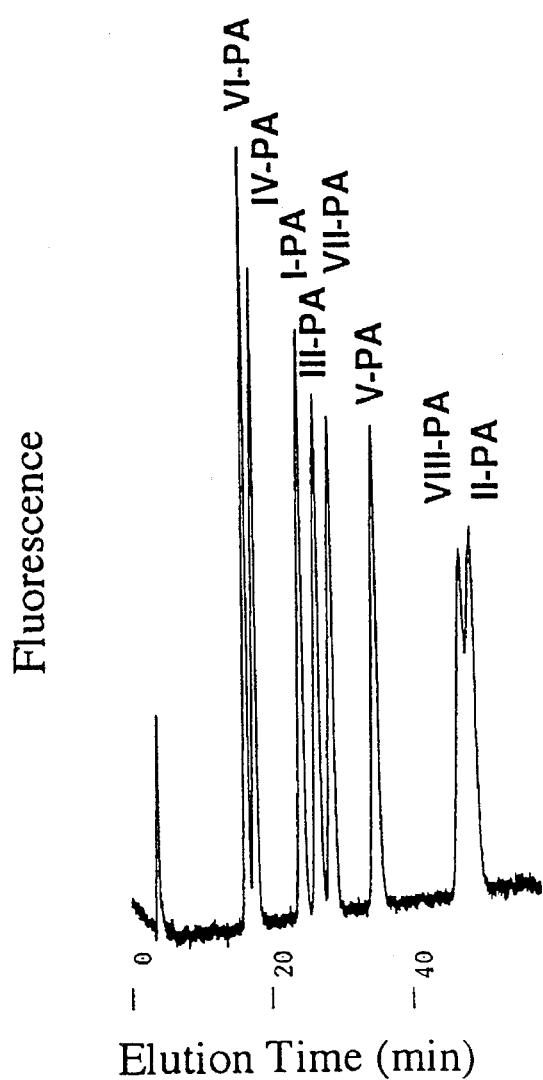
FIG. 1 shows a chart obtained by HPLC of a mixture of 8 oligosaccharides I-PA to VIII-PA under the Condition 1.

(1) separation of I-PA to VIII-PA:

A solution comprising each 1 pmol of I-PA, II-PA and III-PA obtained in Example 1 and commercially available IV-PA (PA Sugar Chain 016; Takara Shuzo), V-PA (PA standard sugar chain 100.1; Nakano Vinegar), VI-PA (PA standard sugar chain 100.2; Nakano Vinegar), VII-PA (PA Sugar Chain 012; Takara Shuzo) and VIII-PA (PA Sugar Chain 013; Takara Shuzo) was treated by HPLC under the Condition 1 (FIG. 1). Eight kinds of the PA-oligosaccharides were separated.

(2) Separation of I-PA to XVI-PA:

1 nmol of XVI-PA (PA Sugar Chain 014; Takara Shuzo) was digested with 1 mU of β-N-acetylglucosaminidase from bovine kidney, which has a comparatively low substrate specificity, in 50 mM phosphate/citrate buffer (pH 5.0) at 37° C. A part of the reaction mixture was analyzed by HPLC with PALPACK TYPE N [eluent: 50 mM acetic acid/triethylamine (pH 7.3); linear gradient from acetonitrile 70% (0 min) to 50% (300 min); other conditions being the same as those of the Condition 1 (hereinafter referred to as "Condition 2")]. When the nondegrated substance had amounted to about 20% of the whole, the reaction mixture was treated at 100° C. for 5 min to terminate the reaction to thereby obtain a mixture of I-PA to XVI-PA.

Figure 2:
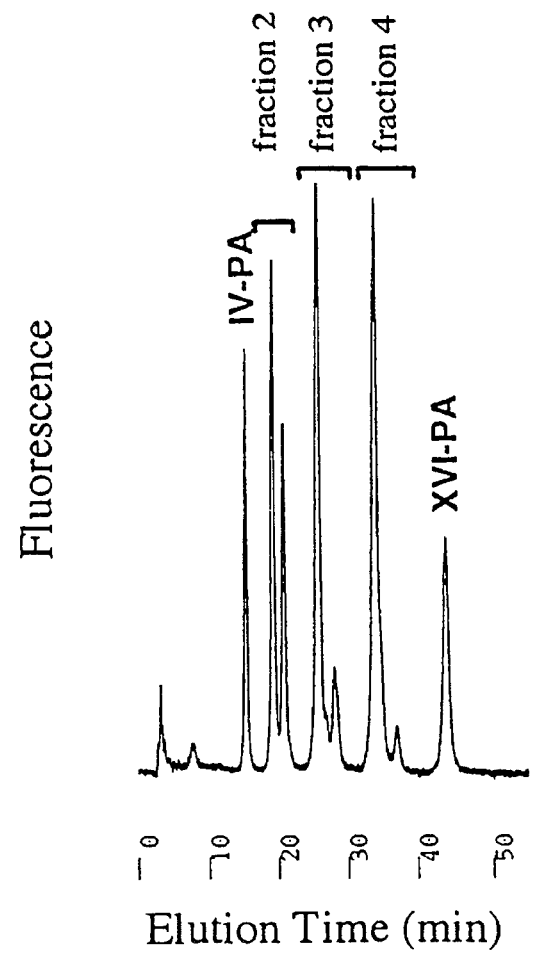
FIG. 2 shows a chart obtained by HPLC of a mixture of 16 ologosaccharides I-PA to XVI-PA under the Condition 2.

The mixture was separated by HPLC under the Condition 2. The obtained chart is given in FIG. 2. The peaks were divided into five fractions, i.e. fraction 1 eluted during the period of 13 to 17 min, fraction 2 during the period of 18 to 23 min, fraction 3 during the period of 24 to 29 min, fraction 4 during the period of 32 to 38 min, and fraction 5 during the period of 42 to 46 min. Under the Condition 2, the sugar chain could be separated on the basis of the number of sugar residues constituting the chain. By comparison with the elution position of the commercially available IV-PA, V-PA, VII-PA, VIII-PA and XVI-PA in HPLC under the Condition 2, it was found that the peak of the fraction 1 obtained at 15.4 min was one in which GN was not linked to the M3 core, namely, it was identified with IV-PA. In the same manner, the fraction 2 was one in which one GN was linked to the M3 core, namely, it was identified with a mixture of four oligosaccharides, i.e. I-PA, V-PA, VI-PA and XII-PA; the fraction 3 was one in which two GN's were linked to the M3 core, namely, it was identified with a mixture of six oligosaccharides, i.e. II-PA, III-PA, VII-PA, IX-PA, XIII-PA and XIV-PA; the fraction 4 was one in which three GN's were linked to the M3 core, namely, it was identified with a mixture of four oligosaccharides, i.e. VIII-PA, X-PA, XI-PA and XV-PA; and the peak of the fraction 5 obtained at 44.0 min was one in which four GN's were linked to the M3 core, namely, it was identified with XVI-PA.

The peak of the fraction 1 obtained at 15.4 min (IV-PA) and that of the fraction 5 obtained at 44.0 min (XVI-PA) appeared as the single peaks of 12.0 min and 15.7 min, respectively, also in HPLC with PALPACK TYPE R [eluent: acetic acid/triethylamine (pH 4.0) containing 0.07% of 1-butanol; other conditions being the same as those of the Condition 1 (hereinafter referred to as "Condition 3")].

Figure 5:
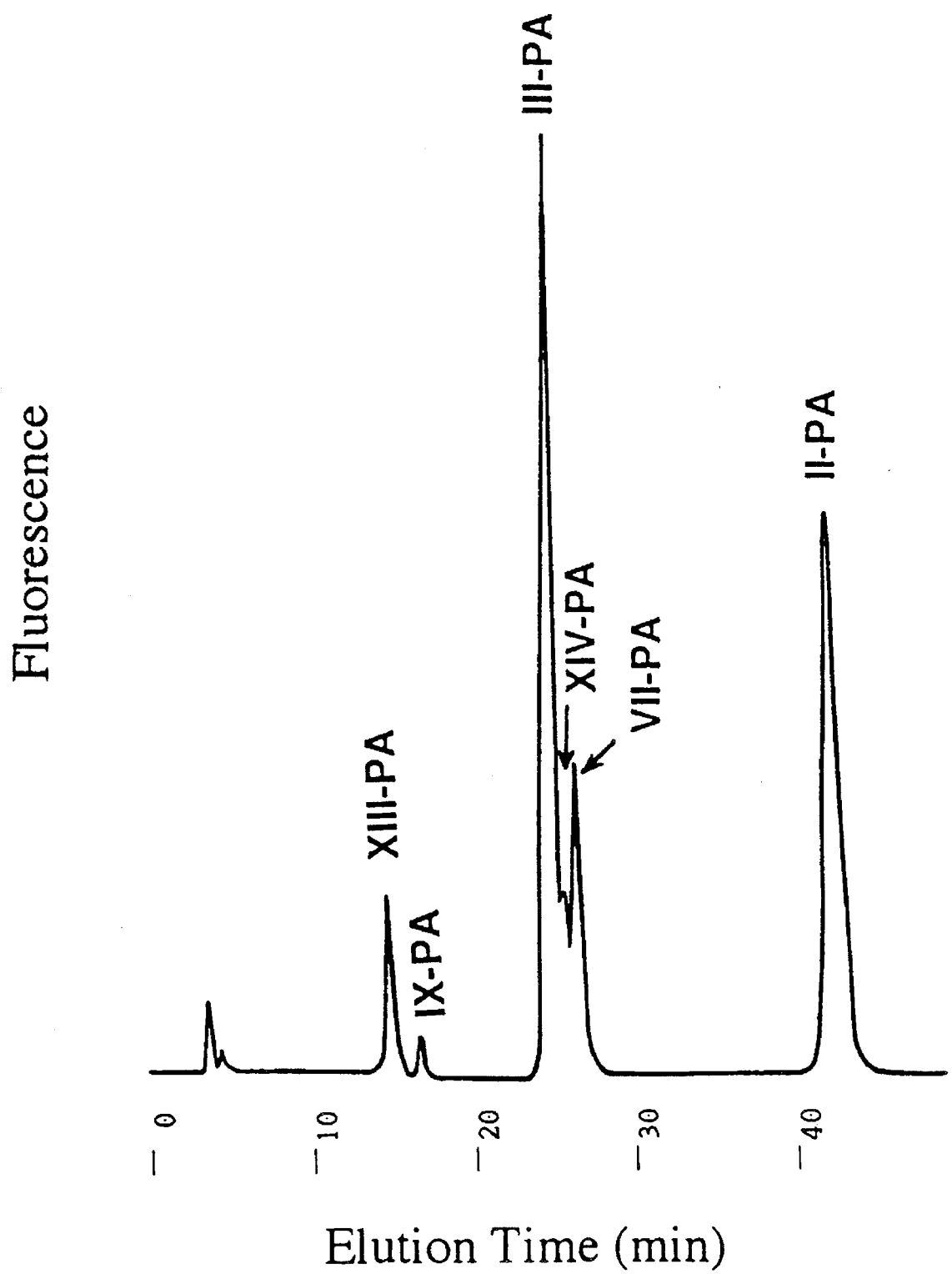
FIG. 5 shows a chart obtained by HPLC of fraction 3 in FIG. 2 under the Condition 1.

When the fraction 2 was separated by HPLC under the Condition 3, VI-PA was eluted at 11.2 min, XII-PA at 12.8 min, I-PA at 15.2 min, and V-PA at 20.7 min. The pattern is given in FIG. 3. When the fraction 3 was analyzed by HPLC under the Condition 1, XIII-PA was eluted at 15.0 min, IX-PA at 16.8 min, III-PA at 25.2 min, XIV-PA at 25.9 min, VII-PA at 26.7 min, and II-PA at 42.5 min. The pattern is given in FIG. 5. When the fraction 4 was analyzed by HPLC under the Condition 3, XV-PA was eluted at 10.4 min, X-PA at 13.3 min, XI-PA at 17.6 min, and VIII-PA at 25.9 min. The pattern is given in FIG. 4. Thus the 16 kinds of the PA-oligosaccharides, I-PA to XVI-PA, could be separated.

The respective peaks were identified as follows. I-PA, II-PA and III-PA obtained in Example 1 and commercially available IV-PA, V-PA, VI-PA, VII-PA, VIII-PA and XVI-PA were used as the standard sugar chains. By comparing the elution positions of the peaks, the peak of 15.4 min in FIG. 2 was identified with IV-PA, that of 44.0 min in FIG. 2 with XVI-PA, that of 11.2 min in FIG. 3 with VI-PA, that of 15.2 min in FIG. 3 with I-PA, that of 20.7 min in FIG. 3 with V-PA, that of 25.9 mim in FIG. 4 with VIII-PA, that of 25.2 min in FIG. 5 with III-PA, that of 26.7 min in FIG. 5 with VII-PA, and that of 42.5 min in FIG. 5 with II-PA.

The peak at 12.8 min in FIG. 3 was identified with XII-PA based on the finding that when it was recovered and then treated with β-N-acetylglucosaminidase from bovine kidney, the M3 core was formed, that the starting material was XVI-PA PA, and that three other oligosaccharides were eluted at different times.

Figure 6:
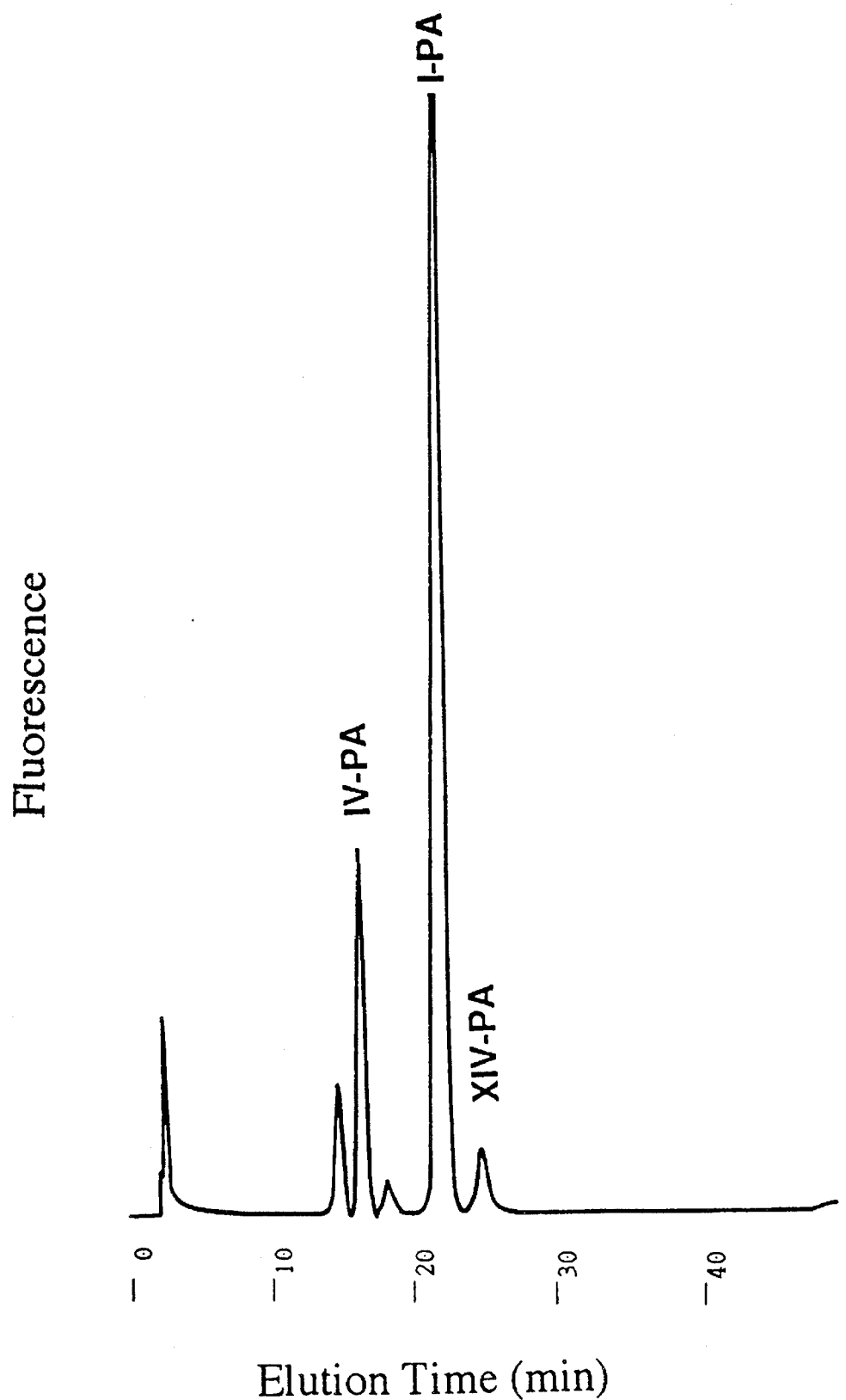
FIG. 6 shows a chart obtained by HPLC of fraction in FIG. 2 under the Condition 1 after the complete digestion with β-N-acetylglucosaminidase from D. pneumoniae.

As for the peaks of the remaining six oligosaccharides, each of them was fractionated and identified by a method which will be described below. The peak of 25.9 min in FIG. 5 was treated as follows: when a part of the fraction 3 was completely digested with β-1,2-linkage-specific β-N-acetylglucosaminidase from D. pneumoniae and then treated by HPLC under the Condition 1, the peaks of 25.2 min (III-PA) and 26.7 min (VII-PA) disappeared (i.e. they were hydrolyzed to form I-PA and IV-PA, respectively), leaving only the peak of 25.9 min (FIG. 6), which was recovered.

The oligosaccharides of the respective peaks thus fractionated were partially digested with β-N-acetylglucosaminidase from bovine kidney and then treated by HPLC under the Condition 2 to separate a fraction in which one GN was linked to the M3 core. The fraction thus recovered was then analyzed by HPLC under the Condition 3. Since V-PA, VI-PA and XII-PA were detected in the digest of the peak of 10.5 min in FIG. 4, the peak was identified with XV-PA. Also, since I-PA, V-PA and XII-PA were detected in the digest of the peak of 13.3 min in FIG. 4, the peak was identified with X-PA. Further, since I-PA, VI-PA and XII-PA were detected in the digest of the peak of 17.6 min in FIG. 4, the peak was identified with XI-PA. Since V-PA and XII-PA were detected in the digest of the peak of 15.0 min in FIG. 5, the peak was identified with XIII-PA. Since VI-PA and XII-PA were detected in the digest of the peak of 16.8 min in FIG. 5, the peak was identified with IX-PA. Since I-PA and XII-PA were detected in the digest of the peak of 25.9 min in FIG. 6, the peak was identified with XIV-PA.

EXAMPLE 3

(1) A mixture of 2.5 μmol of CMP-sialic acid (cytidine 5'-monophospho-N-acetylneuraminic acid, CMP-NANA; Sigma) with 850 nmol of a tetraantennary asialosugar chain (PA-Sugar Chain 004; Takara Shuzo) was reacted with 0.1U of α2,6-sialyltransferase from rat liver (Boehringer Mannheim) in 12.5 mM cacodylate buffer (pH 6.8) containing 0.5% Triton CF-54 at 37° C. for 36 h. In the course of the reaction, 2.5 μmol of CMP-NANA was added to the reaction mixture 16 h and 24 h after the initiation of the reaction.

The reaction mixture was desalted through a Sephadex G-15 column, and the sugar chain fraction was injected to a monoQ column (Pharmacia) and eluted, the gradient being 10 mM to 100 mM ammonium acetate (pH 8.5). A fraction containing 3 mol of sialic acid per mole of the sugar chain was recovered from the eluted fractions. The amount of the recovered sialylated sugar chain was 646 nmol.

500 nmol of the recovered sialylated sugar chain was reacted with 100 U of galactose oxidase from *Dactylium dendoroides* (Takara Shuzo) in the presence of 4.7 mU of catalase (Sigma) in 50 mM phosphate buffer (pH 7.0) at 37° C. for 2 h.

The reaction mixture was treated on a boiling water bath for 10 min to terminate the reaction. Then 1U of sialidase from *A. ureafaciens* (Kyokuto Pharmaceutical) was added to the reaction mixture to conduct digestion at 37° C. for 2 h. Then 250 U of β-galactosidase from Aspergillus (Toyobo) was added to the reaction mixture and the reaction was continued at 37° C. for 5.5 h.

The pH of the reaction mixture was adjusted to about 11 with 5 N sodium hydroxide. 20 mg of sodium borohydride (NaBH$_4$) was added to the reaction mixture, and the resultant mixture was left to stand at room temperature for 30 min. Additional 30 mg of sodium borohydride was added to the reaction mixture, and the resultant mixture was left to stand at room temperature for 30 min to complete the reduction reaction.

The reduction reaction mixture was desalted through a Sephadex G-15 column and then injected to a PALPAK TYPE R column. The elution was conducted with 0.1% 1-butanol and 0.05% trifluoroacetic acid, and the main peak eluting at 30 min was recovered. The resultant sugar chain was XVI-PA in which β-1,6-1linked GN was protected with Gal. The amount of the recovered sugar chain was 300 nmol. A portion (250 nmol) of the protected sugar chain thus obtained was digested with 2.5 U of N-acetylglucosaminidase from bovine kidney in 50 mM citrate buffer (pH 5.0) in presence of 50 mM D-(+)-galactono-1,4-lactone (Nacalai Tesque). After the reaction for 3.5 h, the reaction mixture was treated on a boiling water bath for 10 min to terminate the reaction.

Figure 21:
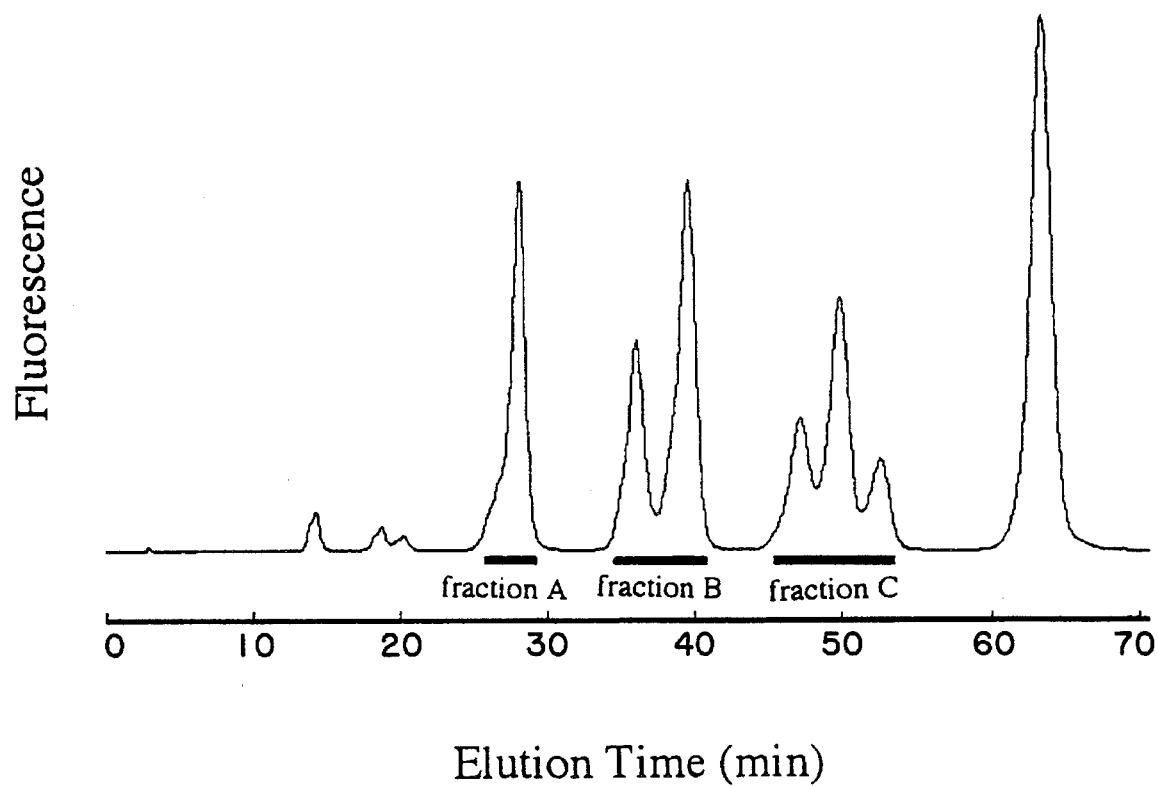
FIG. 21 shows a elution profile of the products obtained by partial digestion of the sugar chain with β-N-acetylglucosaminidase from bovine kidney. The GN residue in the sequence, GN(β1-6)Man(α), in the sugar chain is protected.

The reaction mixture was desalted through a Sephadex G-15 column and three fractions were recovered by HPLC, the conditions are described below, depending on the number of GN units linked to the M3 core (fraction A with one GN unit linked; fraction B with two GN units linked; and fraction C with three GN units linked). The HPLC pattern is shown in FIG. 21.

HPLC conditions:

chromatograph: LC 6A (Shimadzu), column: Asahi PAK NH$_2$ P-50 (6.0 mmφ×150 mm) (Asahi Chemical Industry), eluent A: 50 mM acetic acid/triethylamine containing 75% of acetonitrile (pH 7.3), eluent B: 50 mM acetic acid/triethylamine containing 50% of acetonitrile (pH 7.3), elution: gradient elution wherein the content of eluent B was increased from 10% to 25% during 100 min, detection: fluorescence detector RF-535 (Shimadzu), excitation wavelength: 315 nm, fluorescent wavelength: 380 nm, flow rate: 1 ml/min, and column temp. : 40° C.

Each fraction was digested with 7.5 U of β-galactosidase from Aspergillus at 37° C. for 15 h. Then the digestion mixture was treated on a boiling water bath for 10 min to terminate the reaction and reaction products were separated by HPLC, the conditions of which are described below. XII-PA (23.6 min) was recovered from the reaction product of fraction A; XIII-PA (19.4 min), IX-PA (21.4 min) and XIV-PA (31.3 min) from that of the fraction B; and XV-PA (18.9 min), X-PA (25.4 min) and XI-PA (33.4 min) from that of the fraction C.

HPLC conditions:

chromatograph: LC 6A (Shimadzu), column: YMC Pack AM (10 mmφ×150 mm) (YMC), eluent: 0.05% trifluoroacetic acid containing 0.1% 1-butanol, detection: fluorescence detector RF-535 (Shimadzu), excitation wavelength: 320 nm, fluorescent wavelength: 400 nm, flow rate: 2 ml/min, and column temp. : 40° C.

Then each of six purified oligosaccharides, IX-PA, X-PA, XI-PA, XII-PA, XIII-PA and XIV-PA, were analyzed by mass spectrometry with a API-III mass spectrograph, NMR spectroscopy (in D2O) with a 500 MHz proton nuclear magnetic resonance spectrometer (JEOL) or that of Bruker above-described (only X-PA), and monosaccharide analysis after acid hydrolysis.

Figure 16:
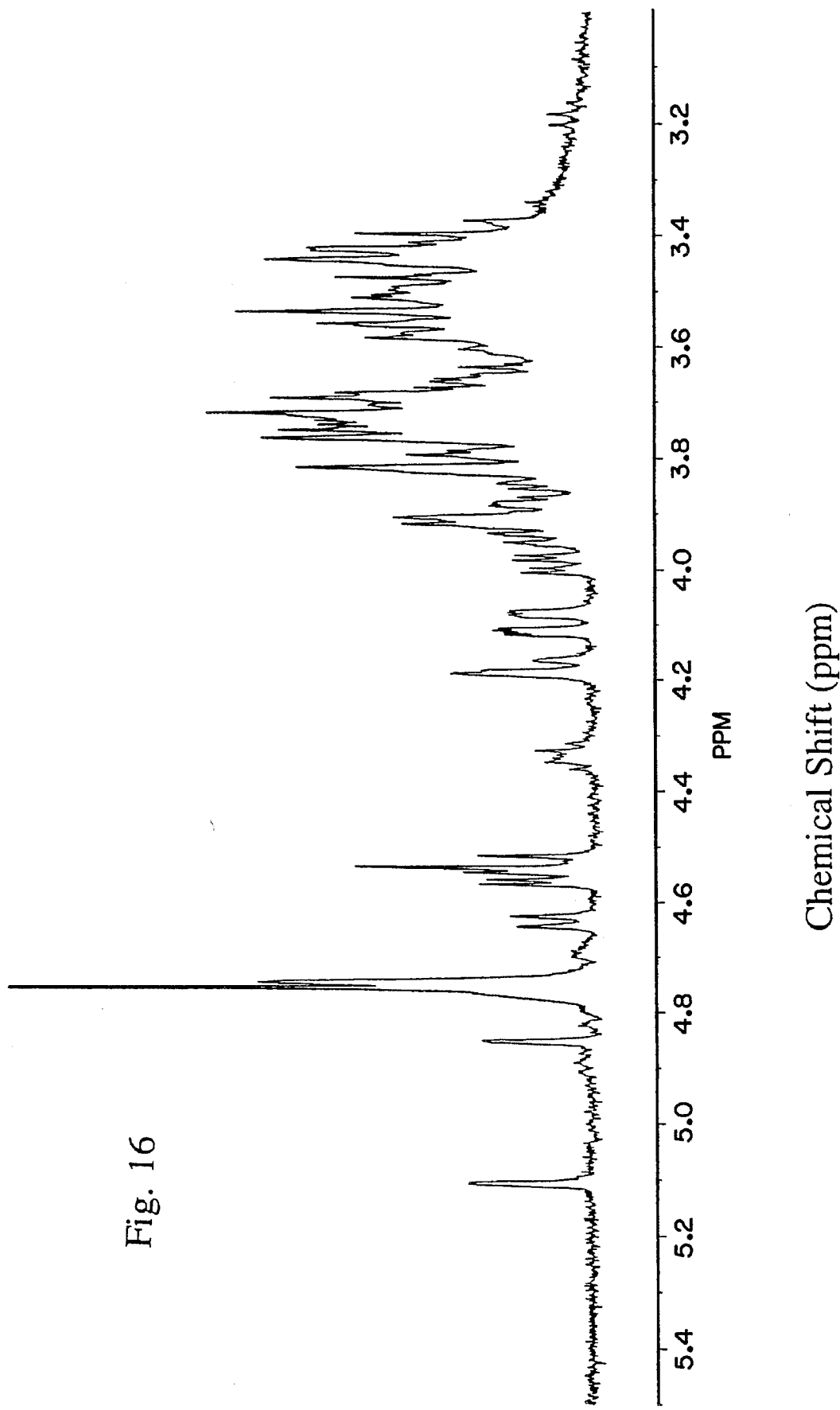
FIG. 16 shows the $^1$H-MNR spectrum, in the range of chemical shift of 3.00 to 5.50 ppm, of X-PA.
Figure 17:
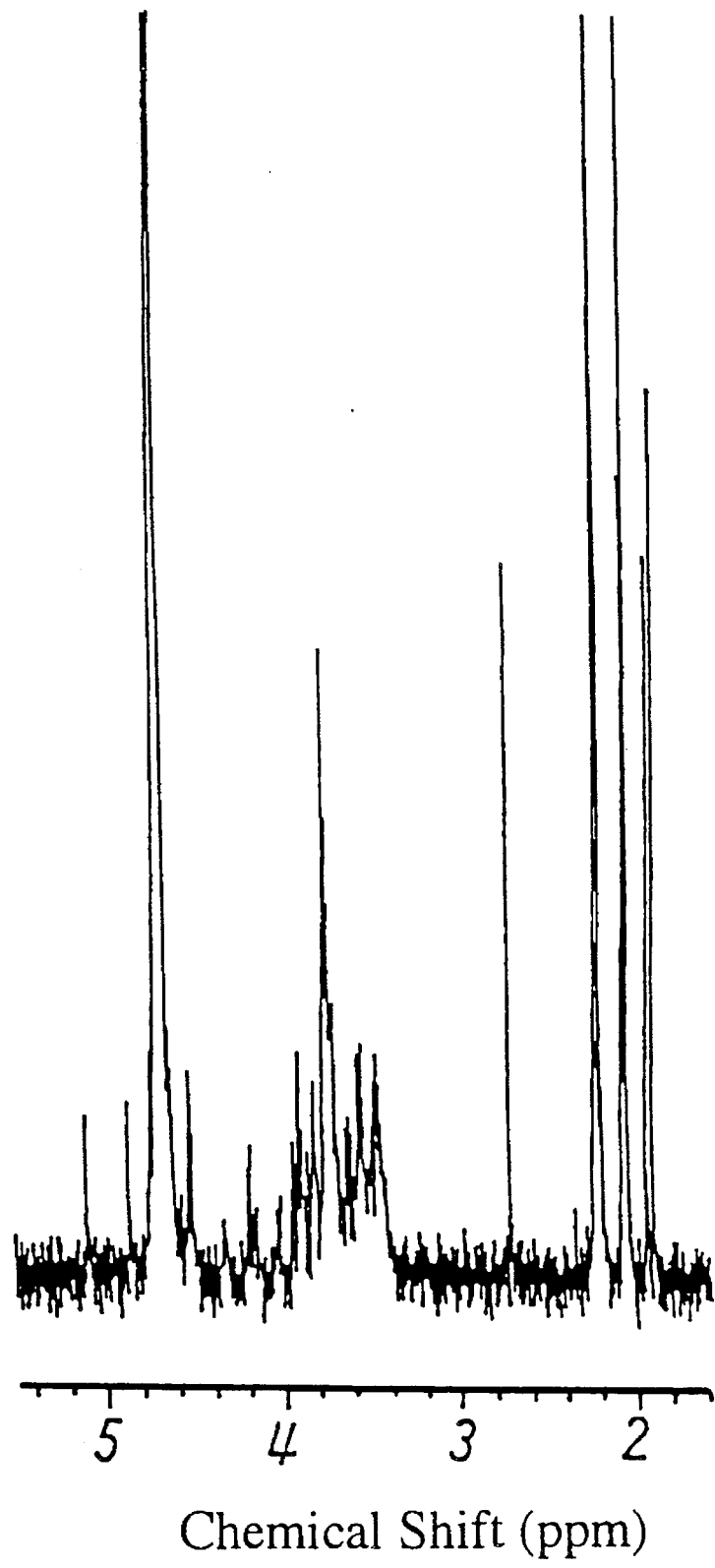
FIG. 17 shows the $^1$H-MNR spectrum, in the range of chemical shift of 1.60 to 5.50 ppm, of XI-PA.
Figure 18:
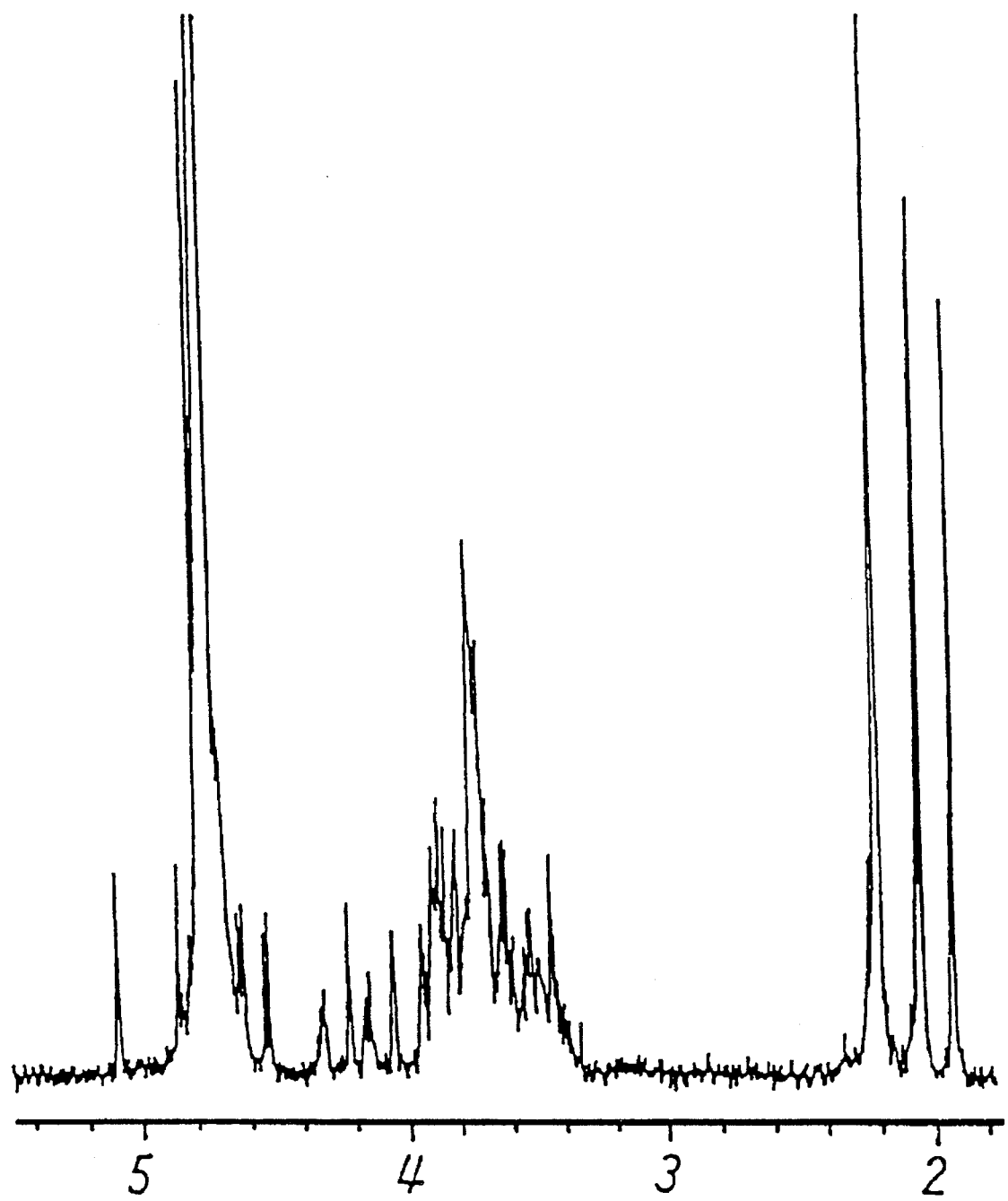
FIG. 18 shows the $^1$H-MNR spectrum, in the range of chemical shift of 1.60 to 5.50 ppm, of XII-PA.
Figure 19:
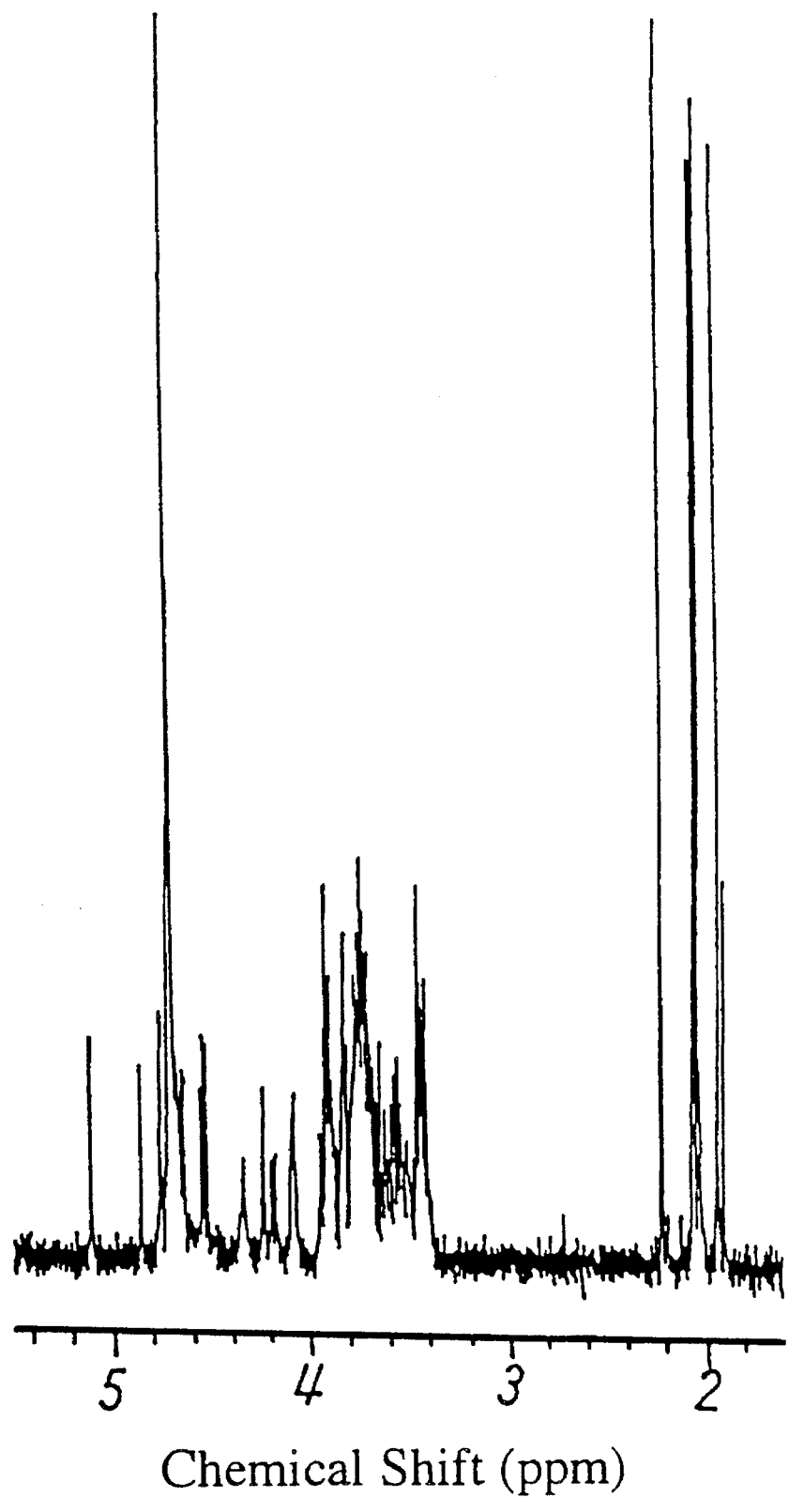
FIG. 19 shows the $^1$H-MNR spectrum, in the range of chemical shift of 1.60 to 5.50 ppm, of XIII-PA.
Figure 20:
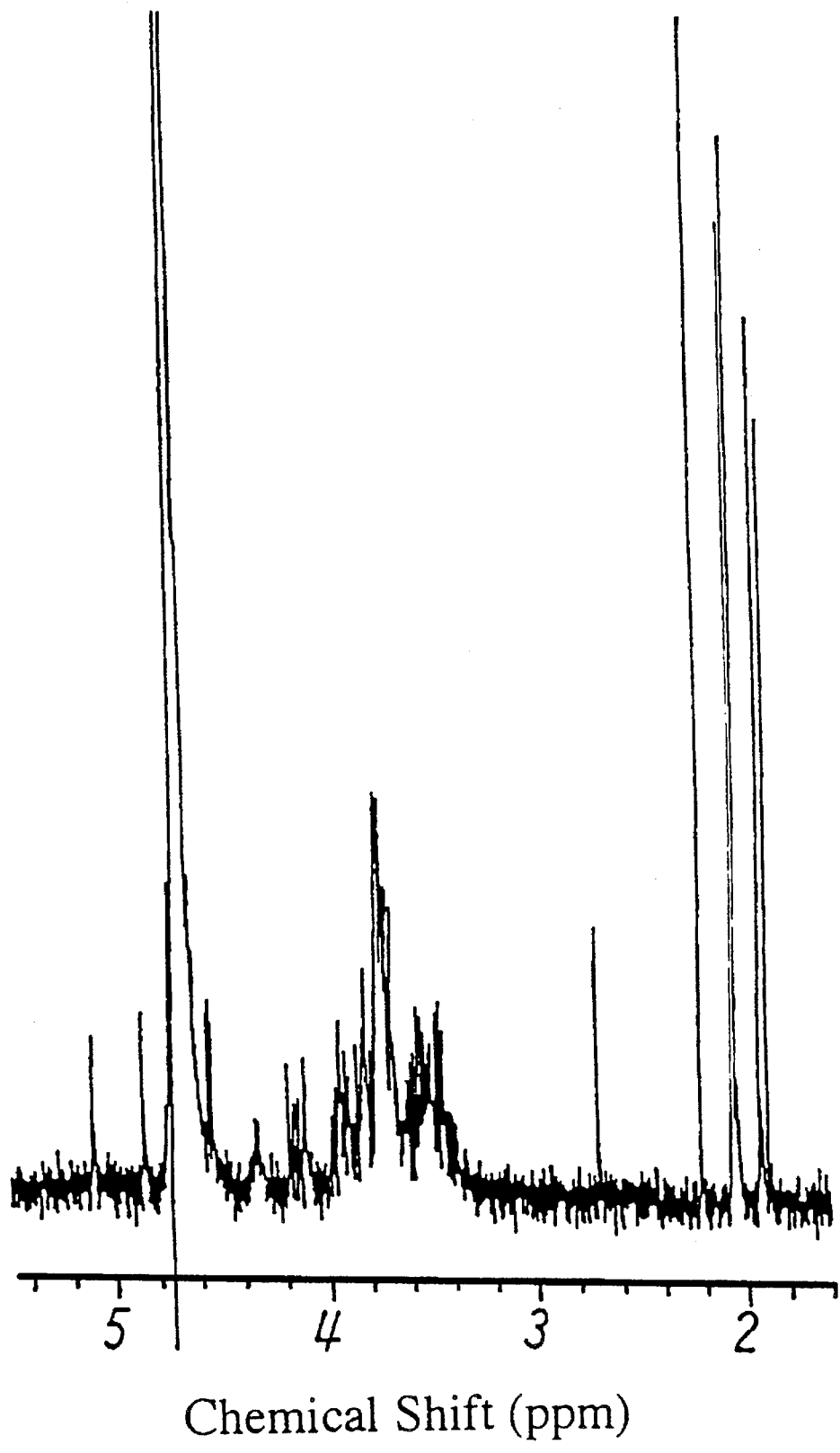
FIG. 20 shows the $^1$H-MNR spectrum, in the range of chemical shift of 1.60 to 5.50 ppm, of XIV-PA.

The properties of the respective oligosaccharides are given below. Further, the $^1$H-NMR spectrum of IX-PA is given in FIG. 14, that of X-PA in FIGS. 15 and 16, that of XI-PA in FIG. 17, that of XII-PA in FIG. 18, that of XIII-PA in FIG. 19, and that of XIV-PA in FIG. 20. The chemical shift values in these $^1$H-NMR spectra are represented by taking the chemical shift value of the methyl proton of acetone in D$_2$O at 37° C. as 2,218 ppm when DSS is used as the standard. In FIGS. 14, 15, 17, 18, 19 and 20, the signal at 2,218 ppm was that of the methyl proton of acetone used as the internal standard.

The reference numerals of the sugar residues in the ¹H-NMR spectra are as shown in the above chemical formula 11.

(Properties of IX-PA)

Mol. wt. 1395.0 (by mass spectrometry) ¹H-NMR 4.552 (H-1, GN-7'), 4.535 (H-1, GN-5), 2.046 (NAc, GN-7'), 2.046 (NAc, GN-5)

Sugar compn. Man: GN=3.0: 3.5, free from Gal and Fuc.

(Properties of X-PA)

Mol. wt. 1599.0 (by mass spectrometry)

¹H-NMR 4.528 (H-1, GN-7'), 4.549 (H-1, GN-5'), 4.557 (H-1, GN-7), 2,028 (NAc, GN-7'), 2. 038 (NAc, GN-5'), 2. 067 (NAc, GN-7 )

Sugar compn. Man: GN=3.0: 4.5, free from Gal and Fuc.

(Properties of XI-PA)

Mol. wt. 1598.0 (by mass spectrometry)

¹H-NMR 4.546 (H-1, GN-7'), 4.515 (H-1, GN-7), 4.529 (H-1, GN-5), 2.045 (NAc, GN-7'), 2.065 (NAc, GN-7), 2.045 (NAc, GN-5)

Sugar compn. Man: GN=3.0: 4.5, free from Gal and Fuc.

(Properties of XII-PA)

Mol. wt. 1191.5 (by mass spectrometry)

¹H-NMR 4.542 (H-1, GN-7'), 2.043 (NAc, GN-7')

Sugar compn. Man: GN=3.0: 2.5, free from Gal and Fuc.

(Properties of XIII-PA)

Mol. wt. 1395.0 (by mass spectrometry)

¹H-NMR 4.530 (H-1, GN-7'), 4.548 (H-1, GN-5'), 2.027 (NAc, GN-7'), 2.038 (NAc, GN-5')

Sugar compn. Man: GN=3.0: 3.5, free from Gal and Fuc.

(Properties of XIV-PA)

Mol. wt. 1395.0 (by mass spectrometry)

¹H -NMR 4.545 (H-1, GN-7'), 4.556 (H-1, GN-7), 2.043 ( NAc, GN- 7 '), 2.065 ( NAc, GN- 7 )

Sugar compn. Man: GN=3.0: 3.5, free from Gal and Fuc.

Figure 7:
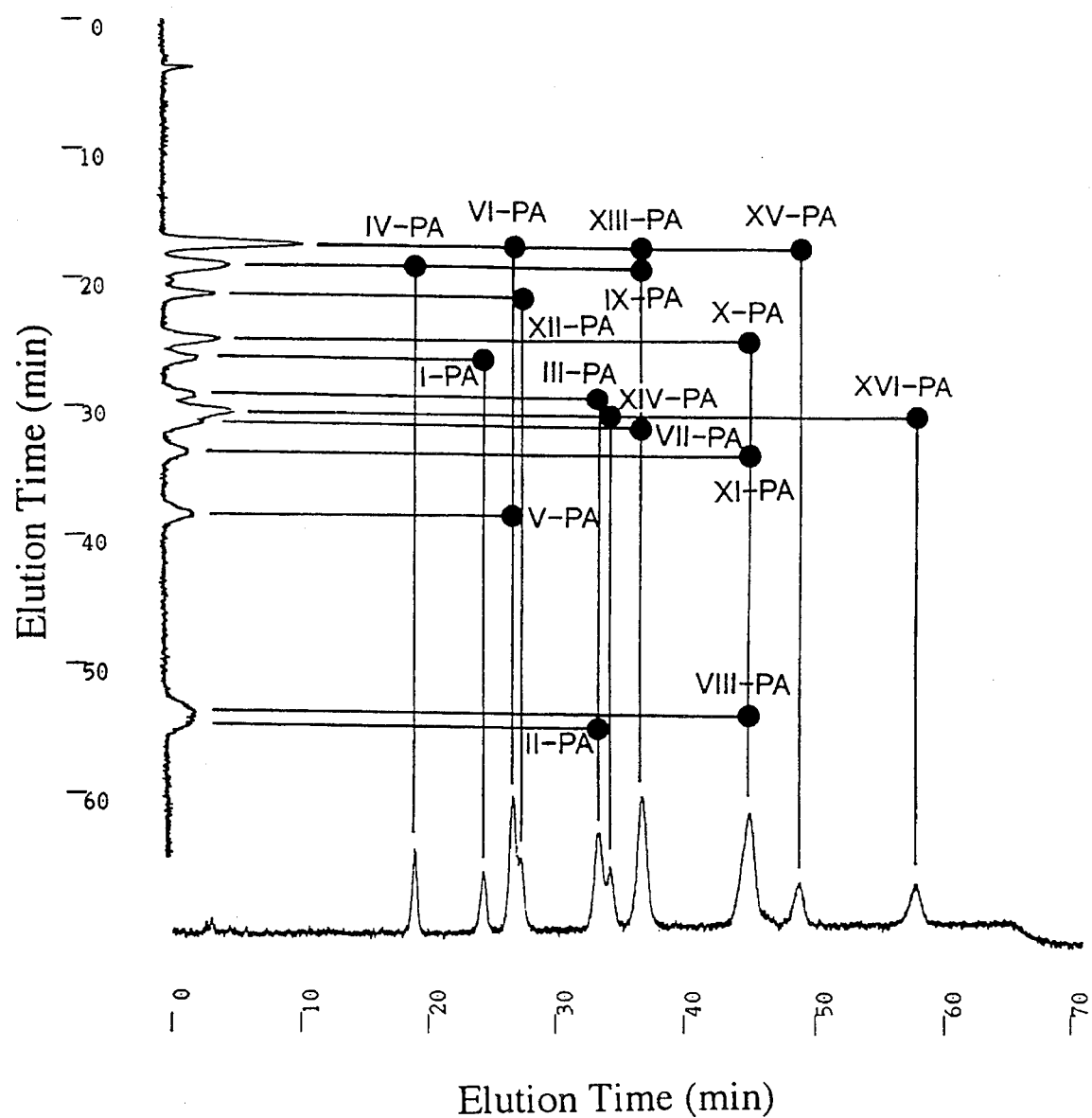
FIG. 7 shows a elution profile of a mixture of 16 oligosaccharides I-PA to XVI-PA under the conditions 2 and 4, and a two-dimensional map thereof.

(2) Two-demensional mapping of oligosaccharides I-PA to XVI-PA:

Each of the sixteen PA-oligosaccharides, I-PA to XVI-PA (500 fmol each), was analyzed by HPLC with two kinds of columns, PALPAK TYPE N column [condition 2], and PALPAK TYPE R column [eluent: 100 mM acetic acid/ triethylamine (pH 4.0) containing 0.02% 1-butanol; other conditions being the same as those of the condition 1 (hereinafter referred to as condition 4)]. The elution profiles of the mixture of the sixteen PA-oligosaccharides on the two columns were shown in FIG. 7. The elution position of each PA-oligosaccharide on the two columns was plotted and thus the two-dimensional sugar map was made. FIG. 7 also shows the two-dimensional sugar map. Final reaction product of this invention can be easily identified by use of this two-dimensional sugar map. Each of the elution time obtained by reversed-phase HPLC (PALPAK TYPE R column) was expressed on the ordinate, and that obtained by size-fractionation HPLC (PALPAK TYPE N column) was expressed on the abscissa.

EXAMPLE 4

Preparation of kit for determination of sugar chain structure:

Kits 1 and 2 for determining the structure of N-acetyl-lactosamine type of sugar chains were prepared (Tables 3 and 4).

The oligosaccharides IV-PA, VII-PA, VIII-PA and XVI-PA to be contained in the kits were the above-mentioned ones produced by Takara Shuzo. Similarly, the oligosaccharides V-PA and VI-PA were those produced by Nakano Vinegar.

The oligosaccharides IX-PA to XV-PA were obtained by the method described in Example 3 or partial hydrolysis of the oligosaccharide XVI-PA with N-acetylglucosaminidase from bovine kideny followed by purification by HPLC by the method described in Example 2- (2).

TABLE 3

Contents of Kit 1 (for 100 runs)

| solution | Reagent | Amount (ml) |
|---|---|---|
| 1 | solution of mixture of oligo-saccharides I-PA to VIII-PA (each 1 pmol/μl) | 0.1 |
| 2 | 250 mM citrate buffer (pH 5.0) | 0.4 |
| 3 | 50 U/ml sialidase from *A. ureafaciens* | 0.5 |
| 4 | 15 U/ml α-2,3-sialidase from *S. typhimurium* | 0.5 |
| 5 | 5 U/ml β-galactosidase from *D. pneumoniae* | 0.5 |
| 6 | 5 U/ml β-galactosidase from Streptococcus | 0.5 |
| 7 | 100 U/ml β-N-acetylglucosaminidase from bovine kidney | 0.5 |
| 8 | 10 U/ml α-fucosidase from bovine kidney | 0.5 |
| 9 | 1 U/ml α-1,3/4-fucosidase derived from Streptomyces | 0.5 |
| 10 | 100 mM acetic acid/triethylamine (pH 4.0) containing 0.035% 1-butanol | 1000 |

| Attachment | | Number |
|---|---|---|
| Column 1: | PALPAK TYPE R (4.6 mmφ × 250 mm) | 1 |

TABLE 4

Contents of Kit 2 (for 100 runs)

| solution | Reagent | Amount (ml) |
|---|---|---|
| 1 | solution of mixture of oligo-saccharides I-PA to VXI-PA (each 1 pmol/μl) | 0.1 |
| 2 | 250 mM citrate buffer (pH 5.0) | 0.4 |
| 3 | 50 U/ml sialidase from *A. ureafaciens* | 0.5 |
| 4 | 15 U/ml α-2,3-sialidase from *S. typhimurium* | 0.5 |
| 5 | 5 U/ml β-galactosidase from *D. pneumoniae* | 0.5 |
| 6 | 5 U/ml β-galactosidase from Streptococcus | 0.5 |
| 7 | 100 U/ml β-N-acetylglucosaminidase from bovine kidney | 0.5 |
| 8 | 10 U/ml α-fucosidase from bovine kidney | 0.5 |
| 9 | 1 U/ml α-1,3/4-fucosidase derived from Streptomyces | 0.5 |
| 10 | 100 mM acetic acid/triethylamine (pH 4.0) containing 0.035% 1-butanol | 1000 |
| 11 | 100 mM acetic acid/triethylamine (pH 4.0) containing 0.07% 1-butanol | 1000 |
| 12-A | 50 mM acetic acid/triethylamine (pH 7.3) containing 75% acetonitrile | 1000 |
| 12-B | 50 mM acetic acid/triethylamine (pH 7.3) containing 50% acetonitrile | 1000 |

| Attachment | | Number |
|---|---|---|
| Column 1: | PALPAK TYPE R (4.6 mmφ × 250 mm) | 1 |
| Column 2: | PALPAK TYPE N (4.6 mmφ × 250 mm) | 1 |

EXAMPLE 5

Bovine fetuin is a glycoprotein having a molecular weight of about 48,000 and about 22% by weight thereof comprises sugar chains. The structure of the sugar chains of the fetuin has been analyzed in detail, so that it is suitable for use in the investigation of the sugar chains of glycoproteins. The main asparagine-binding sugar chains of the fetuin have such a structure that 0 to 5 SA's are linked to the structure of XXII or XXIII in Table 5. The structure of the fetuin varies depending on the number, site and mode of linkage of SA. Since most of the various structures of the fetuin are represented by the formula (6), they could be analyzed with the kit of the present invention.

(1) Preparation of bovine fetuin sugar chain:

1 g of bovine fetuin (Takara Shuzo) was hydrazinolyzed and then the product was N-acetylated to obtain a free sugar chain fraction. This fraction was labeled with 2-aminopyridine. Excess reagents were removed with a Sephadex G15 column (Pharmacia) to obtain the PA sugar chain, which was subjected to the chromatography with DEAE-Toyopearl 650M column (18 mm$\phi$×250 mm; Tosoh) equilibrated with 10 mM tris hydrochloride buffer (pH 9.0) to conduct elution with the NaCl concentration gradient from 0 to 100 mM.

Thus, the PA sugar chain was divided into five fractions wherein 0 to 4 SA's were linked to each molecule. From the five fractions, a fraction having one SA and another fraction having two SA's were used. A part (1/100) of each fraction was separated by HPLC [eluent: 50 mM acetic acid/triethylamine (pH 5.0) containing 0.15% of 1-butanol] with a reversed-phase column Cosmosil 5C$_{18}$AR (4.6 mm$\phi$×250 mm; Nacalai Tesque). A peak of 40 min was prepared from the fraction having one SA linked, and peaks of 38, 48 and 72 min were prepared from that having two SA's linked, and they were further purified by HPLC with ASAHIPAK NH$_2$ P50. The sugar chain in the fraction of 48 min having 2 SA's, that of 38 min having 2 SA's, that of 40 min having 1SA and that of 72 min having 2 SA's will be referred to as A, B, C and D, respectively. Each sugar chain was dissolved in 100 µl of distilled water to prepare a sample solution.

(2) Determination of structure of sugar chain A:

The following operation was conducted with Kit 1 of Example 4:

(Reaction 1) 4 µl of reagent 2, 4 µl of reagent 3, 4 µl of reagent 5 and 3 µl of distilled water were added to 4 µl of the sample to effect a reaction at 37° C. for 5 h. The reaction mixture was treated at 100° C. for 10 min, and 2 µl of the resultant product was analyzed by HPLC under the Condition 1.

(Reaction 2) 4 µl of reagent 2, 4 µl of reagent 5, 4 µl of reagent 7 and 3 µl of distilled water were added to 5 µl of the sample to effect a reaction at 37° C. for 5 h. The reaction mixture was treated at 100° C. for 10 min, and 2 µl of reagent 3 and 2 µl of reagent 5 were added to the mixture to effect a reaction for additional 5 h. The reaction mixture was treated at 100° C. for 10 min, and then 2 µl of the product was analyzed by HPLC in the same manner as that described above.

(Reaction 3) 4 µl of reagent 2, 4 µl of reagent 4, 4 µl of reagent 5 and 4 µl of reagent 7 were added to 5 µl of the sample to effect a reaction at 37° C. for 5 h. The reaction mixture was treated at 100° C. for 10 min and 2 µl of reagent 3 and 2 µl of reagent 5 were added to the mixture to effect a reaction for additional 5 h. The reaction mixture was treated at 100° C. for 10 min, and then 2 µl of the product was analyzed by HPLC in the same manner as that described above.

Results: The reaction mixture obtained by the reaction 1 was analyzed to find out that the product was VIII-PA as judged from the elution time thereof. This suggests that Gal of the sugar chain A was completely removed with β-1,4-linkage linkage-specific β-galactosidase, i.e. the reagent 5 used in the reaction 1. Namely, all the Gal linkages of the sugar chain A were β-1,4-linkage. Therefore, the sugar chain (A) was determined to be one wherein $1_1=m_1=m'_2=m'_3=m'_4=q=p_1=p_2=p_3=p_4=0$, and $1_2=1_3=1_4=m_2=m_3=m_4=1$ in the formula (6). Then, the reaction mixture obtained by the reaction 2 was analyzed to find out that the product was III-PA as judged from the elution time thereof. Thus, the sugar chain A had SA in two Gal's which were linked to the two GN's on the α-1,3-linked Man of the PA oligosaccharide XXII (XXII-PA) in Table 5. Namely, $n_1=n_2=n'_1=n'_2=0$ and $n_3+n'_3=n_4+n'_4=1$ in the formula (6). Thereafter, the reaction mixture obtained by the reaction 3 was analyzed to find that the product comprised about 80% of VI-PA and about 20% of III-PA as judged from the elution time thereof. Thus, the sugar chain A was determined to be composed of about 20% of chains which have SA linked through α-2,6 to both of two Gal's to which SA had been proved to be linked by the result above, in other words, wherein $n_3=1$ and $n_4=1$, and about 80% of chains which have SA linked through α-2,6 to the only Gal linked to the GN(β1-2)Man(α1-3), in other words, wherein $n_3=0$ and $n_4=1$. As a result, the sugar chain A was determined to be a mixture of XXIV-PA and XXV-PA in a ratio of about 4:1, each having a structure given in Table 5.

(3) Determination of structure of sugar chain B:

The following operation was conducted with Kit 1 of Example 4:

(Reaction 1) 4 µl of reagent 2, 4 µl of reagent 3, 4 µl of reagent 5 and 3 µl of distilled water were added to 5 µl of the sample to effect a reaction at 37° C. for 5 h. The reaction mixture was treated at 100° C. for 10 min, and 2 µl of the resultant product was analyzed by HPLC in the same manner as in item (2).

(Reaction 2) 4 µl of reagent 2, 4 µl of reagent 5, 4 µl of reagent 7 and 3 µl of distilled water were added to 5 µl of the sample to effect a reaction at 37° C. for 5 h. The reaction mixture was treated at 100° C. for 10 min and 2 µl of reagent 3 and 2 µl of reagent 5 were added to the mixture to effect a reaction for additional 5 h. The reaction mixture was treated at 100° C. for 10 min, and then 2 µl of the product was analyzed by HPLC in the same manner as that described above.

(Reaction 3) 4 µl of reagent 2, 4 µl of reagent 4, 4 µl of reagent 5 and 4 µl of reagent 7 were added to 5 µl of the sample to effect a reaction at 37° C. for 5 h. The reaction mixture was treated at 100° C. for 10 min and 2 µl of reagent 3 and 2 µl of reagent 5 were added to the mixture to effect a reaction for additional 5 h. The reaction mixture was treated at 100° C. for 10 min, and then 2 µl of the product was analyzed by HPLC in the same manner as that described above.

Results: The reaction mixture obtained by the reaction 1 was analyzed to find out that the product was VII-PA as judged from the elution time thereof. Therefore, the sugar chain B was determined to be one wherein $1_1=1_3=m_1=m_3=m'_1=m'_3=q=p_1=p_2=p_3=p_4=0$, and $1_2=1_4=m_2=m_4=1$ in the formula (6). Then, the reaction mixture obtained by the reaction 2 was analyzed to find out that the product was VII-PA as judged from the elution time thereof. Thus, the sugar chain B was determined to be one which had SA in both Gal's in the PA oligosaccharide XXIII (XXIII-PA) in Table 5, in other words, wherein $n_2+n'_2=n_4+n'_4=1$ in the formula (6). Thereafter, the reaction mixture obtained by the reaction 3 was analyzed to find out that the product was VI-PA as judged from the elution time thereof. Thus, the sugar chain B was determined to be one which had α-2,6-linked SA on the branch of Man which was linked through α-1,3-linkage in the XXIII-PA, in other words, wherein $n_2=0$ and $n_4=1$. As a result, the sugar chain B was determined to be XXVI-PA in Table 5.

(4) Determination of structure of sugar chain C:

The following operation was conducted with Kit 1 of Example 4:

(Reaction 1) 4 μl of reagent 2, 4 μl of reagent 3, 4 μl of reagent 5 and 3 μl of distilled water were added to 5 μl of the sample to conduct a reaction at 37° C. for 5 h. The reaction mixture was treated at 100° C. for 10 min, and 2 μl of the resultant product was analyzed by HPLC in the same manner as that of item (2).

(Reaction 2) 4 μl of reagent 2, 4 μl of reagent 5, 4 μl of reagent 7 and 3 μl of distilled water were added to 5 μl of the sample to effect a reaction at 37° C. for 5 h. The reaction mixture was treated at 100° C. for 10 min and 2 μl of reagent 3 and 2 μl of reagent 5 were added to the mixture to effect a reaction for additional 5 h. The reaction mixture was treated at 100° C. for 10 min, and then 2 μl of the product was analyzed by HPLC in the same manner as that described above.

(Reaction 3) 4 μl of reagent 2, 4 μl of reagent 4, 4 μl of reagent 5 and 4 μl of reagent 7 were added to 5 μl of the sample to effect a reaction at 37° C. for 5 h. The reaction mixture was treated at 100° C. for 10 min and 2 μl of reagent 3 and 2 μl of reagent 5 were added to the mixture to effect a reaction for additional 5 h. The reaction mixture was treated at 100° C. for 10 min, and then 2 μl of the product was analyzed by HPLC in the same manner as that described above.

Results: The reaction mixture obtained by the reaction 1 was analyzed to find out that the product was VIII-PA as judged from the elution time thereof. Therefore, the sugar chain C was determined to be one wherein $1_1m_1=m'_1=m'_2=m'_3=m'_4=q=p_1=p_2=p_3=p_4=0$, and $1_2=1_3=1_4=m_2=m_3=m_4=1$ in the formula (6). Then, the reaction mixture obtained by the reaction 2 was analyzed to find out that the product comprised about 50% of I-PA and about 50% of V-PA as judged from the elution time thereof. Thus, the sugar chain C was determined to be a nearly 1:1 mixture of an oligosaccharide which had SA linked to the Gal linked to the GN(β1-4)Man(α1-3) of XXII-PA, in other words, wherein $n_2=n_4=n'_2=n'_4=0$ and $n_3+n'_3=1$ in the formula (6) and an oligosaccharide having SA linked to the Gal linked to the GN(β1-2)Man(α1-6), in other words, wherein $n_3=n_4=n'_3=n'_4=0$ and $n_2+n'_2=1$ in the formula (6). Thereafter, the reaction mixture obtained by the reaction 3 was analyzed to find out that the product was IV-PA as judged from the elution time thereof. Thus, the sugar chain C was determined to be one which did not have SA linked through α-2,6 but SA's all linked through α-2,3, in other words, wherein $n'_2=1$ or $n'_3=1$ in the formula (6). As a result, the purified sugar chain C was determined to be a nearly 1:1 mixture of XXVII-PA and XXVIII-PA in Table 5.

(5) Determination of structure of sugar chain D:

The following operation was conducted with Kit 1 of Example 4:

(Reaction 1) 4 μl of reagent 2, 4 μl of reagent 3, 4 μl of reagent 5 and 3 μl of distilled water were added to 5 μl of the sample to effect a reaction at 37° C. for 5 h. The reaction mixture was treated at 100° C. for 10 min, and 2 μl of the resultant product was analyzed by HPLC in the same manner as that of item (2).

(Reaction 2) 4 μl of reagent 2, 4 μl of reagent 5, 4 μl of reagent 7 and 3 μl of distilled water were added to 5 μl of the sample to effect a reaction at 37° C. for 5 h. The reaction mixture was treated at 100° C. for 10 min and 2 μl of reagent 3 and 2 μl of reagent 5 were added to the mixture to effect a reaction for additional 5 h. The reaction mixture was treated at 100° C. for 10 min, and then 2 μl of the product was analyzed by HPLC in the same manner as that described above.

Results: The reaction mixture obtained by the reaction 1 was analyzed to find out that the product was VIII-PA as judged from the elution time thereof. Therefore, the sugar chain D was determined to be one wherein $1=m_1=m'_1=m'_2=m'_3=m'_4=q=p_1=p_2=p_3=p_4=0$, and $1_2=1_3=1_4=m_2=m_3=m_4=1$ in the formula (6). Then, the reaction mixture obtained by the reaction 2 was analyzed to find out that the product was II-PA as judged from the elution time thereof. Thus, the sugar chain D was determined to be one which had SA linked to the Gal linked to the GN(β1-4)Man(α1-3) and also SA linked to the Gal linked to the GN(β1-2)Man(α1-6) of XXII-PA, in other words, wherein $n_2+n'_2=n_3+n'_3=1$ in the formula (6). Therefore, the sugar chain D was determined to be XXIX-PA in Table 5.

The oligosaccharides XXII to XXIX satisfy the conditions relating to variables $1_x$, $m_x$, $m'_x$, $n_x$, $n'_x$, q and $p_x$ (x being 1, 2, 3 or 4) in the formula (6) given in the following Table 5. And XXII-PA to XXIX-PA are obtained by labeling the oligosaccharides XXII to XXIX respectively with 2-aminopyridine.

TABLE 5

| oligo-saccharides | oligosaccharides derived from bovine fetuin — valiables |||||||||||||||||||||||
|---|---|---|---|---|---|---|---|---|---|---|---|---|---|---|---|---|---|---|---|---|---|---|---|---|
| | $l_1$ | $m_1$ | $m'_1$ | $n_1$ | $n'_1$ | $l_2$ | $m_2$ | $m'_2$ | $n_2$ | $n'_2$ | $l_3$ | $m_3$ | $m'_3$ | $n_3$ | $n'_3$ | $l_4$ | $m_4$ | $m'_4$ | $n_4$ | $n'_4$ | q | $p_1$ | $p_2$ | $p_3$ | $p_4$ |
| XXII | 0 | 0 | 0 | 0 | 0 | 1 | 1 | 0 | 0 | 0 | 1 | 1 | 0 | 0 | 0 | 1 | 1 | 0 | 0 | 0 | 0 | 0 | 0 | 0 | 0 |
| XXIII | 0 | 0 | 0 | 0 | 0 | 1 | 1 | 0 | 0 | 0 | 0 | 0 | 0 | 0 | 0 | 1 | 1 | 0 | 0 | 0 | 0 | 0 | 0 | 0 | 0 |
| XXIV | 0 | 0 | 0 | 0 | 0 | 1 | 1 | 0 | 0 | 0 | 1 | 1 | 0 | 0 | 1 | 1 | 1 | 0 | 1 | 0 | 0 | 0 | 0 | 0 | 0 |
| XXV | 0 | 0 | 0 | 0 | 0 | 1 | 1 | 0 | 0 | 0 | 1 | 1 | 0 | 1 | 0 | 1 | 1 | 0 | 1 | 0 | 0 | 0 | 0 | 0 | 0 |
| XXVI | 0 | 0 | 0 | 0 | 0 | 1 | 1 | 0 | 0 | 1 | 0 | 0 | 0 | 0 | 0 | 1 | 1 | 0 | 1 | 0 | 0 | 0 | 0 | 0 | 0 |
| XXVII | 0 | 0 | 0 | 0 | 0 | 1 | 1 | 0 | 0 | 1 | 1 | 1 | 0 | 0 | 0 | 1 | 1 | 0 | 0 | 0 | 0 | 0 | 0 | 0 | 0 |
| XXVIII | 0 | 0 | 0 | 0 | 0 | 1 | 1 | 0 | 0 | 0 | 1 | 1 | 0 | 0 | 1 | 1 | 1 | 0 | 0 | 0 | 0 | 0 | 0 | 0 | 0 |
| XXIX | 0 | 0 | 0 | 0 | 0 | 1 | 1 | 0 | (1) | | 1 | 1 | 0 | (1) | | 1 | 1 | 0 | 0 | 0 | 0 | 0 | 0 | 0 | 0 |

In the above Table 5, the symbol (1) represents that one of the two variables is 1 and the other is 0.

EXAMPLE 6

The sugar chain fraction was obtained from 1 mg of $\alpha_1$-acid glycoprotein (Sigma) by hydrazinolysis and N-acetylation.

The fraction was treated with 0.1N HCl for 1 h to remove SA residues, and then the mixture was chromatographed on Bio-Gel P-4 (Bio-Rad) column (25 mm×900 mm×2). Sugar chains were eluted with $H_2O$, and the fractions with the elution position corresponding to that of isomaltooligosaccharide (DP=21), of which the degree of polimerization was 21, were pooled and lyophilized. The pooled fraction was labeled with 2-aminopyridine. PA-oligosacharides were purified by HPLC with PALPAK TYPE R column and then sugar chain E was obtained.

50 pmol of sugar chain E were digested with 5 mU of endo-$\beta$-galactosidase from *Escherichia freundii* at 37° C. for 2 h, and a portion was analyzed by HPLC with an amide-silica column [*Anal. Biochem.* 171, 73–90, (1988)]. The product peak was eluted about 2.5 glucose units earlier than sugar chain E. This product was named sugar chain F.

From these results, sugar chain E might have a N-acetyllactosamine unit in a certain branch of a sugar chain represented by the formula (6) with the variables, $(1_1=1_2=1_3=1_4=m_1=m_2=m_3=m_4=1$, and the rest are 0), i.e. so-called tetraantennary sugar chain. Endo-$\beta$-galactosidase might release Gal($\beta$1-4)GN($\beta$1-3)Gal from sugar chain E producing sugar chain F.

The branch having N-acetyllactosamine unit was determined with Kit 2 of Example 4.

(Reaction 1) Sugar chain F, 10 pmol/5 μl, was mixed with 4 μl of reagent 2, 2 μl of reagent 5, and 9 μl of distilled water, and the mixture was incubated at 37° C. for 2 h. After the mixture was boiled at 100° C. for 10 min to stop the reaction, 2 μl of the mixture was analyzed by HPLC under the conditions of 2 and 4.

(Reaction 2) Sugar chain F, 10 pmol/5 μl, was mixed with 4 μl of reagent 2, 4 μl of reagent 7, and 7 μl of distilled water, and the mixture was incubated at 37° C. for 2 h. After the mixture was boiled at 100° C. for 10 min to stop the reaction, 2 μl of reagent 5 was added to the mixture and the mixture was incubated for 2 h. After the mixture was boiled at 100° C. for 10 min to stop the reaction, 2 μl of the mixture was analyzed by HPLC under the conditions of 2 and 4.

Results: The product from the reaction 1 was identified with XVI-PA judging from the elution position of the product and standard sugar chain in HPLC under the conditions of 2 and 4. Thus sugar chain F should be represented by the formula (6) with the variables, $(1_1=1_2=1_3=1_4=1)$. The product from the reaction 2 was identified with XI-PA in the same way, and thus sugar chain F was identified with a sugar chain represented by the formula (6) with the variables, $(m_1=m_3=m_4=1, m_2=0)$. From these results, sugar chain F was represented by the formula (6) with the variables, $(1_1=1_2=1_3=1_4=m_1=m_3=m_41$, and the rest were 0). The results also show that N-acetyllactosamine unit was linked to Gal linked to the GN($\beta$1-2)Man($\alpha$1-6).

EFFECT OF THE INVENTION

The present invention provides a more exact, reliable, and simple method for determining the sugar chain structure, a kit to be used for said method, and novel oligosaccharides useful for said method as standards.

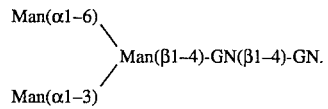

What is claimed is:

1. A method for determining the structure of an N-acetyllactosamine sugar chain in a sample containing said sugar chain, which comprises determining the site of linkage and the mode of linkage of sugar residues at the non-reducing terminal side of a $\beta$-N-acetylglucosamine residue linked to an $\alpha$-mannose residue in M3 core by means of detecting the presence of the $\beta$-N-acetylglucosamine residue after enzymatic or chemical digestion of said sugar chain, said M3 core having the formula

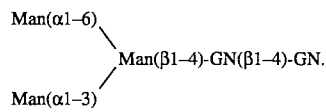

2. A method of claim 1, which is conducted with the use of a kit containing at least one oligosaccharide represented by the following chemical formula 1:

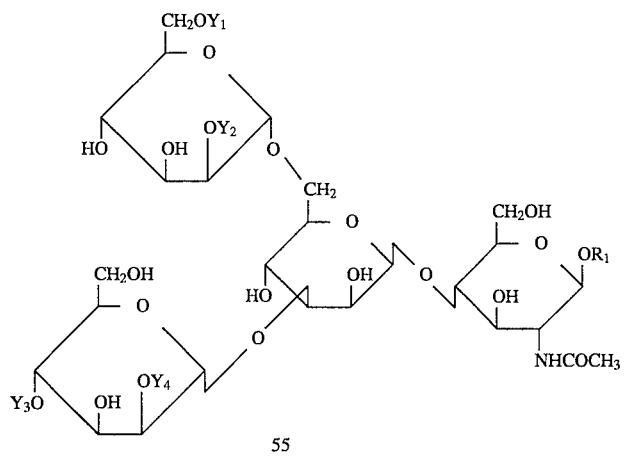

[chemical formula 1]

wherein $Y_1$, $Y_2$, $Y_3$ and $Y_4$ represent hydrogen or a $\beta$-N-acetylglucosamine residue, and $R_1$ is represented by the following chemical formula 2 or 3:

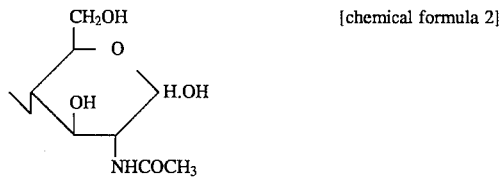

[chemical formula 2]

-continued

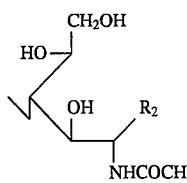

[chemical formula 3]

wherein $R_2$ represents an aldehyde group, a labeled methylene group or a labeled methine group.

3. A method of claim 2, wherein the β-N-acetylglucosamine residues of step (1) do not have a specified sugar residue at the non-reducing terminal side, wherein the site of linkage and the mode of linkage of the specified sugar residue is determined.

4. A method of claim 3, wherein the sugar residues are removed by enzymatic treatment.

5. A method of claim 4, wherein the enzymatic treatment is digestion with glycosidases.

6. A method of claim 5, wherein the glycosidases are selected from the group consisting of β-N-acetylglucosaminidase, β-galactosidase, sialidase and α-fucosidase.

7. A method of claim 6, wherein at least one of the glycosidases is a linkage-specific glycosidase.

8. A method of claim 7, wherein the linkage-specific glycosidase is selected from the group consisting of β-1,3-linkage-specific β-galactosidase, β-1,4-linkage-specific β-galactosidase, α-2,3-linkage-specific sialidase, α-2,6-linkage-specific sialidase, α-1,3/4-linkage-specific α-fucosidase and α-1,2-linkage-specific α-fucosidase.

9. A method of claim 2, wherein the β-N-acetylglucosamine residues of step (1) have a specified sugar residue at the non-reducing terminal side, wherein the site of linkage and the mode of linkage of the specified sugar residue is determined.

10. A method of claim 9, wherein the sugar residues are removed by enzymatic treatment.

11. A method of claim 10, wherein the enzymatic treatment is digestion with glycosidases.

12. A method of claim 11, wherein the glycosidases are selected from the group consisting of β-N-acetylglucosaminidase, β-galactosidase, sialidase, α-fucosidase, lacto-N-biosidase and endo-β-galactosidase.

13. A method of claim 12, wherein at least one of the glycosidases is a linkage-specific glycosidase.

14. A method of claim 13, wherein the linkage-specific glycosidase is selected from the group consisting of β-1,3-linkage-specific β-galactosidase, β-1,4-linkage-specific β-galactosidase, α-2,3-linkage-specific sialidase, α-2,6-linkage-specific sialidase, α-1,3/4-linkage-specific α-fucosidase and α-1,2-linkage-specific α-fucosidase.

15. A method of claim 14, wherein $R_1$ is represented by the chemical formula 3.

16. A method of claim 15, wherein R2 represents a labeled methylene group.

17. A method of claim 16, wherein the labeled methylene group is a methylene group labeled with 2-aminopyridine.

18. An oligosaccharide represented by the following chemical formula 4:

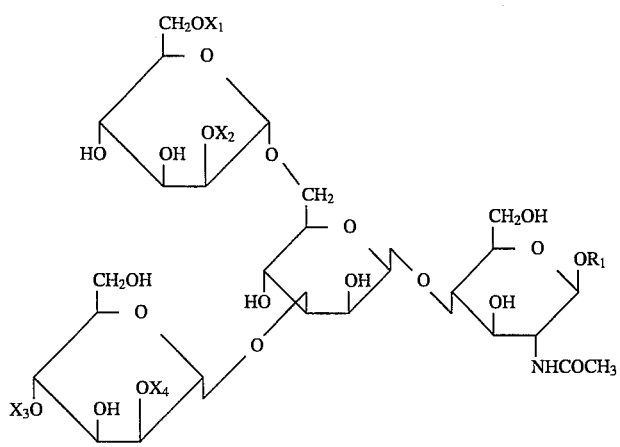

chemical formula 4 wherein $X_1$, $X_2$, $X_3$ and $X_4$ represent hydrogen or a β-N-acetylglucosamine residue with the proviso that the case where both $X_1$ and $X_3$ represent hydrogen simultaneously or the case where both $X_2$ and $X_4$ represent β-N-acetylglucosamine residues simultaneously is excepted, and $R_1$ is represented by the following chemical formula 2 or 3:

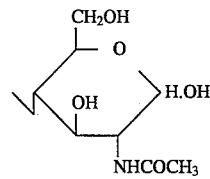

chemical formula 2

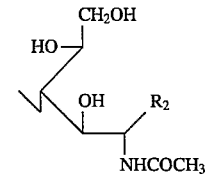

chemical formula 3 wherein $R_2$ represents an aldehyde group, a labeled methylene group or a labeled methine group.

19. An oligosaccharide of claim 18, wherein $R_1$ is represented by the chemical formula 3.

20. An oligosaccharide of claim 19, wherein $R_2$ represents a labeled methylene group.

21. An oligosaccharide of claim 20, wherein the labeled methylene group is a methylene group labeled with 2-aminopyridine.

22. A method for determining the structure of an N-acetyl-lactosamine sugar chain in a sample containing said sugar chain, which comprises the following steps:

(1) removing β-N-acetylglucosamine residues linked to an α-mannose residue in M3 core selectively, (2) removing the remaining sugar residues at the non-reducing terminal side of a β-N-acetylglucosamine residue linked to an α-mannose residue in M3 core provided that the sugar residues still remain in the sugar chain obtained by step (1), and (3) identifying the resulting products of step (1) or (2) by comparing them with standard sugar chains, said M3 core having the formula